(12) United States Patent
Shah et al.

(10) Patent No.: US 8,956,651 B2
(45) Date of Patent: Feb. 17, 2015

(54) ORAL FORMULATIONS AND LIPOPHILIC SALTS OF METHYLNAL TREXONE

(71) Applicant: Wyeth, LLC, Madison, NJ (US)

(72) Inventors: Syed M. Shah, Delray Beach, FL (US); Christopher Richard Diorio, Campbell Hall, NY (US); Eric C. Ehrnsperger, New City, NY (US); Xu Meng, San Diego, CA (US); Kadum A. Al Shareffi, North Potomac, MD (US); Jonathan Marc Cohen, Monroe, NY (US)

(73) Assignee: Wyeth, LLC, Madison, NJ (US)

( * ) Notice: Subject to any disclaimer, the term of this patent is extended or adjusted under 35 U.S.C. 154(b) by 0 days.

(21) Appl. No.: 13/966,779

(22) Filed: Aug. 14, 2013

(65) Prior Publication Data
US 2013/0330407 A1    Dec. 12, 2013

Related U.S. Application Data

(63) Continuation of application No. 13/045,108, filed on Mar. 10, 2011, now Pat. No. 8,524,276.

(60) Provisional application No. 61/313,018, filed on Mar. 11, 2010.

(51) Int. Cl.
| | | |
|---|---|---|
| *A61K 9/20* | (2006.01) | |
| *A61K 31/485* | (2006.01) | |
| *C07D 489/08* | (2006.01) | |
| *A61K 9/28* | (2006.01) | |
| *A61K 47/12* | (2006.01) | |
| *A61K 47/20* | (2006.01) | |

(52) U.S. Cl.
CPC .............. *A61K 31/485* (2013.01); *A61K 9/2054* (2013.01); *A61K 9/2077* (2013.01); *C07D 489/08* (2013.01); *A61K 9/28* (2013.01); *A61K 9/2013* (2013.01); *A61K 47/12* (2013.01); *A61K 47/20* (2013.01)
USPC .......................................... 424/465; 514/282

(58) Field of Classification Search
None
See application file for complete search history.

(56) References Cited

U.S. PATENT DOCUMENTS

| | | | |
|---|---|---|---|
| 5,972,954 A | 10/1999 | Foss et al. | |
| 6,274,591 B1 | 8/2001 | Foss et al. | |
| 6,419,959 B1 | 7/2002 | Walter et al. | |
| 6,559,158 B1 | 5/2003 | Foss et al. | |
| 6,608,075 B2 | 8/2003 | Foss et al. | |
| 2003/0144510 A1 | 7/2003 | Gala et al. | |
| 2003/0187010 A1 | 10/2003 | Foss et al. | |
| 2004/0162306 A1 | 8/2004 | Foss et al. | |
| 2006/0177380 A1* | 8/2006 | Emigh et al. ................. | 424/10.1 |
| 2008/0070975 A1 | 3/2008 | Shah et al. | |
| 2010/0087472 A1 | 4/2010 | Foss et al. | |
| 2012/0190702 A1 | 7/2012 | Foss et al. | |
| 2012/0277260 A1 | 11/2012 | Foss et al. | |
| 2014/0249171 A1 | 9/2014 | Shah et al. | |

FOREIGN PATENT DOCUMENTS

| | | |
|---|---|---|
| WO | WO 94/08599 | 4/1994 |
| WO | WO 2004/091665 A1 | 10/2004 |
| WO | WO 2006/127899 A2 | 11/2006 |
| WO | WO 2008/021394 A2 | 2/2008 |
| WO | WO 2008/121860 A1 | 10/2008 |
| WO | WO 2008121352 | 10/2008 |
| WO | 2009/137086 A1 | 11/2009 |
| WO | WO 2010/039851 | 4/2010 |

OTHER PUBLICATIONS

Bastin, R. J. et al.: "Salt Selection and Optimisation for Pharmaceutical New Chemical Entities", Organic Process Research and Development, Cambridge, GB, vol. 4, No. 5; Jan. 1, 2000; pp. 427-435.

Langguth P. et al., "Intestinal absorption of the quaternary trospium chloride: permeability-lowering factors and bioavailabilities for oral dosage forms." *Eur J Pharm Biopharm* 43:265-272 (1997).

Langguth P. et al., "Lipophilisation of hydrophilic compounds, consequences on transepidermal and intestinal transport of trospium chloride." *Arzneimittelforschung* 37:1362-1366 (1987).

European Search Report for European Application No. 11157837.3 dated Jun. 24, 2011.

International Search Report for International Patent Application No. PCT/US11/27913 dated Jul. 15, 2011.

Berge, S.M. et al. "Pharmaceutical Salts," Journal of Pharmaceutical Sciences, 1977, vol. 66, No. 1, pp. 1-19.

* cited by examiner

*Primary Examiner* — Michael G Hartley
*Assistant Examiner* — Robert Cabral
(74) *Attorney, Agent, or Firm* — McCarter & English, LLP; Jonathan M. Sparks; Maneesh Gulati

(57) ABSTRACT

The present invention provides compositions comprising methylnaltrexone or a salt thereof, and compositions and formulations thereof, for oral administration.

31 Claims, 8 Drawing Sheets

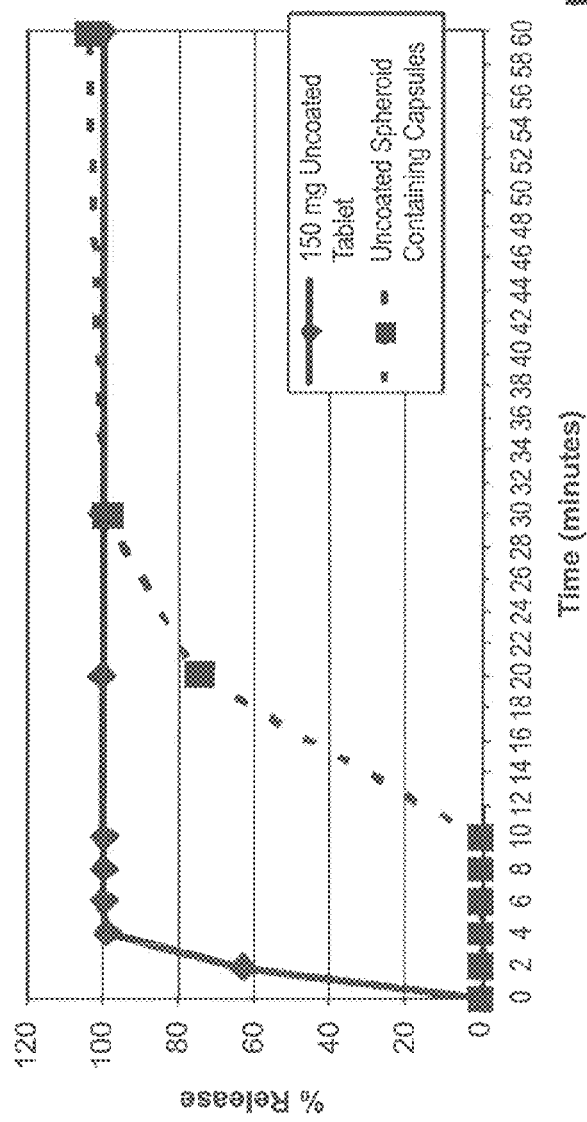
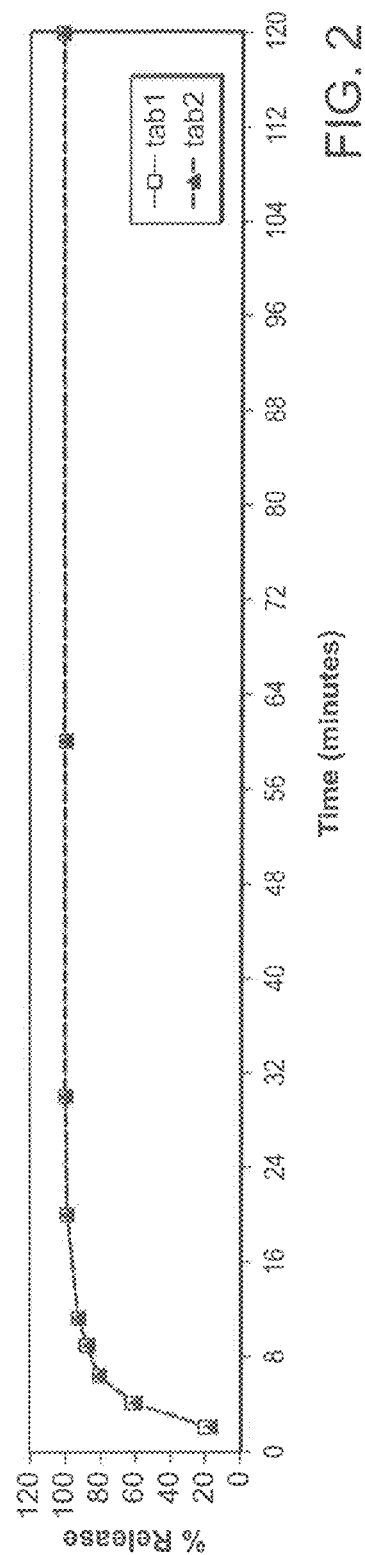
FIG. 1
FIG. 2

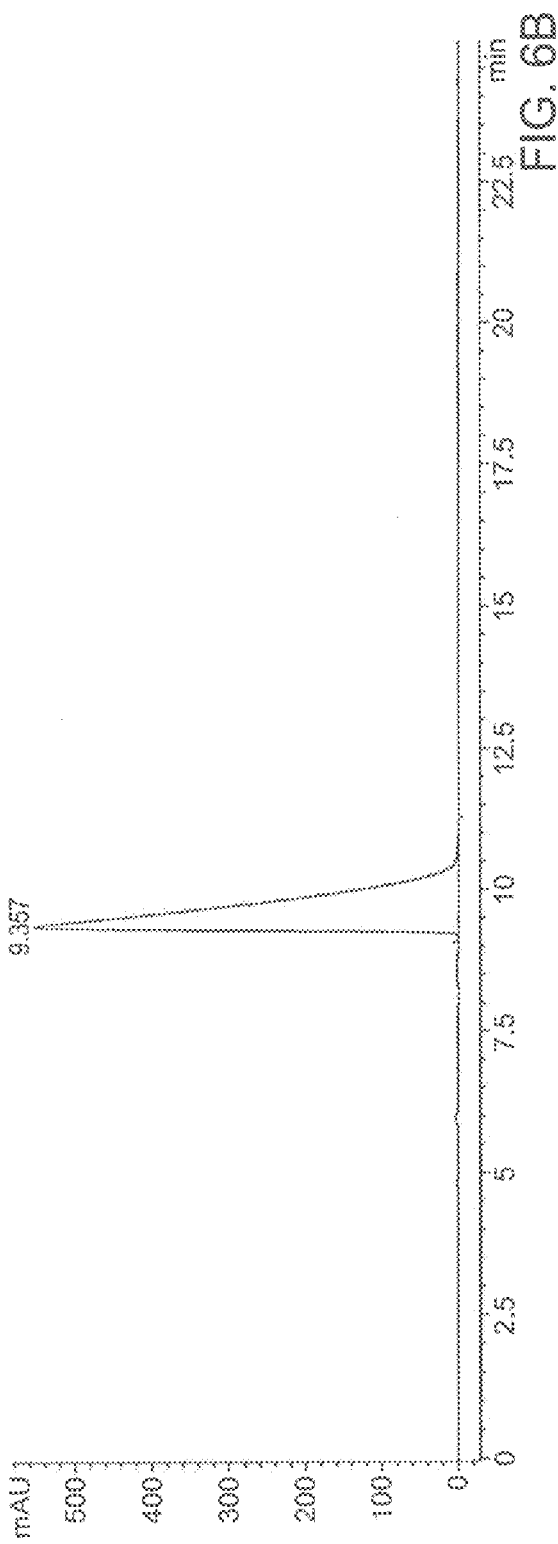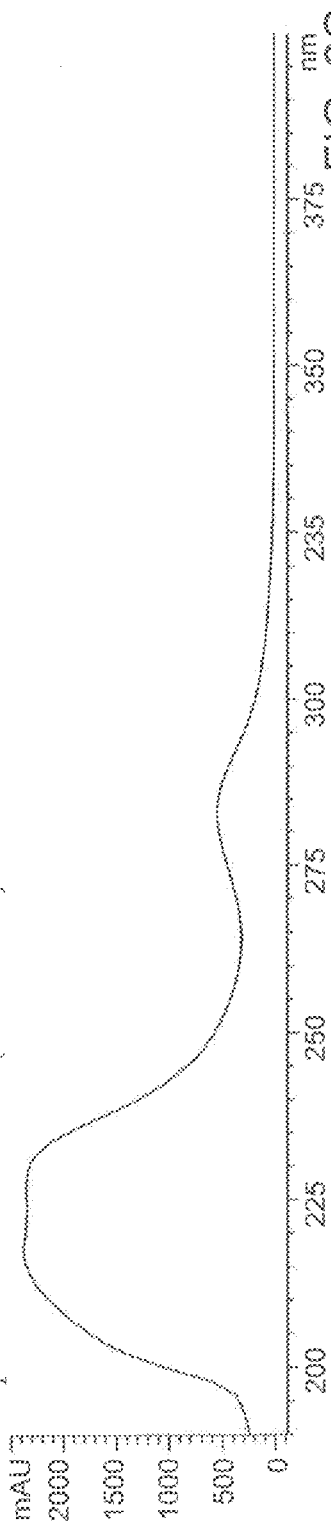

120
ORAL FORMULATIONS AND LIPOPHILIC SALTS OF METHYLNALTREXONE

RELATED APPLICATIONS

This application is a continuation of U.S. patent application Ser. No. 13/045,108, filed on Mar. 10, 2011, which claims the benefit of U.S. Provisional Application No. 61/313,018, filed Mar. 11, 2010, the entire contents of which are hereby incorporated by reference herein.

BACKGROUND OF THE INVENTION

Opioids are widely used in treating patients with pain. Such patients include those with advanced cancers and other terminal diseases and also those with chronic non-malignant pain and acute non-malignant pain. Opioids are narcotic medications that activate opioid receptors located in the central nervous system to relieve pain. Opioids, however, also react with receptors outside of the central nervous system, resulting in side effects including constipation, nausea, vomiting, urinary retention, and severe itching. Notable are the effects of opioids in the gastrointestinal (GI) tract where these drugs inhibit gastric emptying and peristalsis in the intestines, thereby decreasing the rate of intestinal transit and producing constipation. The use of opioids in treating pain is often limited due to these undesired side effects, which can be debilitating and often cause patients to refuse the use of opioid analgesics.

In addition to exogenous opioid-induced side effects, studies have suggested that endogenous opioids and opioid receptors may also affect the gastrointestinal (GI) tract and may be involved in normal regulation of intestinal motility and mucosal transport of fluids. Thus, an abnormal physiological level of endogenous opioids and/or receptor activity may also lead to bowel dysfunction. For example, patients who have undergone surgical procedures, especially surgery of the abdomen, often suffer from a particular bowel dysfunction, termed post-operative ileus, that may be caused by fluctuations in natural opioid levels. Similarly, women who have recently given birth commonly suffer from post partum ileus, which may be caused by similar fluctuations in natural opioid levels as a result of birthing stress. Gastrointestinal dysfunction associated with post-operative or post-partum ileus can typically last for 3 to 5 days, with some severe cases lasting more than a week. Administration of opioids to a patient after surgery to treat pain, which is now an almost universal practice, may exacerbate bowel dysfunction, thereby delaying recovery of normal bowel function, prolonging hospital stays, and increasing medical care costs.

Opioid receptor antagonists, such as naloxone, naltrexone, and nalmefene, have been studied as a means of antagonizing the undesirable peripheral side effects of opioids. However, these agents not only act on peripheral opioid receptors but also on opioid receptors in the central nervous system, sometimes reversing the beneficial and desired analgesic effects of opioids or causing symptoms of opioid withdrawal. Preferable approaches for use in controlling opioid-induced side effects include administration of peripheral acting opioid receptor antagonists that do not readily cross the blood-brain barrier.

The peripheral μ opioid receptor antagonist methylnaltrexone has been studied since the late 1970s. It has been used in patients to reduce opioid-induced side effects such as constipation, pruritus, nausea, and urinary retention (see, e.g., U.S. Pat. Nos. 5,972,954, 5,102,887, 4,861,781, and 4,719,215; and Yuan et al., *Drug and Alcohol Dependence* 1998, 52, 161). The dosage form of methylnaltrexone used most often in these studies has been a solution of methylnaltrexone for intravenous injection.

In U.S. Pat. No. 6,559,158, the dose of methylnaltrexone for treating methadone maintenance patients was explored. It was hypothesized in the '158 patent, based on studies of methadone maintenance patients, that patients taking opioids chronically would be responsive to doses of methylnaltrexone that were previously considered to be too low to be clinically efficacious. (Methadone maintenance patients typically have an addiction to opiates such as heroin, oxycontin, dilaudid or hydrocone. They would have a history of a stable dose of methadone treatment for at least 30 days of greater than or equal to 30 mg/day, and more typically higher.) Low doses of methylnaltrexone were administered intravenously. These doses were between 0.01 and 0.37 mg/kg, wherein average peak plasma levels of 162 (30-774 ng/ml) were reported. These intravenous doses in methadone maintenance patients induced "immediate" laxation.

Methylnaltrexone subcutaneous injection was explored and has been clinically approved in the United States to treat opioid-induced constipation in patients with advanced medical illness who are receiving palliative care. The subcutaneous injection dose found to be effective was 0.15 or 0.3 mg/kg. This dose did not induce "immediate" laxation, but rather induced laxation within 4 hours in a significant number of patients treated.

Attempts have been made to make an oral dosage form of certain opioid antagonists, including methylnaltrexone. In U.S. Pat. No. 6,419,959, an oral dosage form is constructed so as to release certain compounds "over the whole gastrointestinal tract." According to the '959 patent, opioid antagonists are not always suitable for administration in an immediate release form due to dose limiting side effects. In addition, opioid-induced constipation was believed to result from the direct and local effects of opioids on receptors across the entire gastrointestinal tract. To address these issues, the '959 patent suggests dosing certain opioid antagonists, including methylnaltrexone, in a controlled-release dosage form, thereby delivering these antagonists at acceptable doses locally across the entire gastrointestinal tract. Data respecting methylnaltrexone specifically, however, was not reported.

In U.S. Pat. No. 6,274,591, it was demonstrated that an enteric coated methylnaltrexone which released substantially no methylnaltrexone in the stomach was more effective in antagonizing the oral-cecal delay caused by morphine than was an uncoated methylnaltreone. The '591 patent suggests and claims delivering effective amounts of methylnaltrexone using an oral dosage that by-passes the stomach altogether. Data respecting laxation, however, was not reported.

In U.S. Pat. No. 6,559,158, an oral dose of methylnaltrexone was explored for treating constipation in methadone maintenance patients (i.e., patients shown to be highly sensitive to the effects of methylnaltrexone). The dose of methylnaltrexone administered orally in a capsule was 0.3-3.0 mg/kg. Methylnaltrexone capsules administered to these patients induced laxation in the several patients tested, although over periods of time between 1.2 and 24 hours depending on the dose. The fastest response was seen in the four patients receiving 3.0 mg/kg (5.2+/−4.5 hours, with a range of 1.2-10 hours).

Accordingly, the need exists for bioavailable oral dosage formulations comprising methylnaltrexone.

SUMMARY OF THE INVENTION

Capsules containing enterically coated spheroids of a formulation of methylnaltrexone were tested in patients suffering from opioid-induced constipation. The patients in this study were receiving opioids for non-malignant pain. (They were not chronic methadone maintenance patients.) Patients were administered 300 mg or 450 mg of enterically coated methylnaltrexone capsules (approximately 4 mg/kg and 6 mg/kg, respectively), which were doses within the ranges reported to be effective in the '591 patent. The average peak plasma level of methylnaltrexone resulting from the 300 mg dose was less than 10 ng/mL and the average peak plasma level of methylnaltrexone resulting from the 450 mg dose was less than 20 ng/mL. These preparations unexpectedly were not effective for treating opioid-induced constipation. They did not induce laxation and did not cause more bowel movements in patients relative to controls. This was surprising in view of the teachings in the art.

Based on the results of the enterically coated methylnaltrexone capsules, it was unclear whether achieving laxation depended on the peak plasma levels of the drug, the timing of achieving the plasma levels of the drug, or other factors such as a local effect. Further experiments were conducted, and as a result, the inventors turned their attention to developing an oral formulation containing methylnaltrexone that was not enterically coated.

Capsules containing spheroids of a formulation of methylnaltrexone, but without the enteric coating, were tested in patients receiving opioids for non-malignant pain. Doses of 150 mg, 300 mg, 450 mg, and 600 mg were tested. These doses resulted in average peak plasma levels of between about 15 and 40 ng/ml. These capsules without the enteric coating did not induce laxation and did not cause more bowel movements in this patient population relative to controls.

Tablets containing spheroids of a formulation of methylnaltrexone, without an enteric coating, were tested in patients receiving opioids for non-malignant pain. Doses of 150 mg, 300 mg, 450 mg, and 600 mg were tested. These doses resulted in average peak plasma levels of between about 7 and 40 ng/ml, similar to the peak plasma levels achieved with the uncoated capsules. These tablets without an enteric coating showed activity with statistical significance at one dose, but did not consistently induce laxation across all doses. That there was activity with a tablet but not a capsule would have been surprising to one of ordinary skill in the art based on the information available in the prior art.

The prior art did not make clear what would be required to create an oral methylnaltrexone effective for treating opioid induced constipation in patients receiving opioids for non-malignant pain. First, the prior art did not make clear whether achieving laxation depended on the overall plasma levels of the drug, the peak plasma levels of the drug, or the timing of achieving the plasma levels of the drug. Second, even if the pharmacokinetics for achieving laxation were established, the prior art did not make clear formulation methodology for predictably controlling the pharmacokinetics of oral methylnaltrexone, other than via dose alterations and coatings. Because of the desire to further improve the performance of the non-enteric coated tablet, further formulation development studies were undertaken.

Methylnaltrexone is hydrophilic and quite soluble in aqueous solutions. The positive charge of the quaternary amine causes methylnaltrexone to be poorly absorbed in the gastrointestinal tract. In general, less than about 5% of methylnaltrexone is absorbed into the bloodstream when delivered orally.

There are many possible general approaches to increasing the absorption of an orally administered drug. It was unknown, however, which approach might result in an improvement of the efficacy of oral methylnaltrexone. The inventors tested tablet formulations, capsule formulations, liquid formulations, gap junction openers, Pgp inhibitors, active transport agents, oil suspensions, effervescent solutions for rapid release, and others. Most of the approaches attempted did not improve absorption in the laboratory models used. In fact, when tested in certain dog models, some of the approaches had the opposite of the anticipated effect, that is, absorption was inhibited in one or more of the tested parameters.

Ion pairing has been investigated to reduce the apparent ionic charge on a molecule. The interaction between a hydrophilic, charged molecule and an amphiphilic counter ion can make the hydrophilic molecule sufficiently lipophilic to enable (or increase) solubility of the molecule in a non-aqueous solvent. Since ion pairing increases partitioning of the molecule into an organic phase, much of the work in this area has been directed towards extraction of ionic molecules into organic solvents, separation of molecules by chromatography, reaction of hydrophilic molecules in organic solvents, and so forth. With respect to drug absorption, most of the work has been limited to delivery of a drug to the skin, eyes, nasal cavity, or vaginal cavity (see, e.g., J. Hadgraft, "Skin Deep," *European Journal of Pharmaceutics and Biopharmaceutics* 58, 291-299, 2004; Quintanar-Guerrero et al., Application of the Ion-Pair Concept to Hydrophilic Substances with Special Emphasis on Peptides," *Pharmaceutical Research* 14, 119-127, 1997). There has been only limited work reported on in the prior art for improving the bioavailability of orally administered drugs using ion pairs.

An ion pair between the positively charged methylnaltrexone and a negatively charged moiety was postulated by the inventors to make a "pair" that is more hydrophobic than methylnaltrexone bromide and thereby enhance the absorption of methylnaltrexone in the stomach. Various ion pairs were formed using methylnaltrexone and anions. One such ion pair was formed between methylnaltrexone and dodecyl (lauryl) sulfate.

It was discovered, unexpectedly, that methylnaltrexone and an amphiphilic pharmaceutically acceptable excipient, that forms an ion pair or salt with methylnaltrexone when dissolved in solution, in a solid dosage form together with a rapid-acting disintegrant (e.g., a carbon dioxide-generating disintegrant) was effective to induce laxation.

Without wishing to be bound by any particular theory of the invention, it is believed that there is a local gastric effect and a systemic effect, which combine to achieve laxation when using the formulations and preparations of the invention. Such a dual effect could suggest that laxation can be achieved using the oral formulations of the invention at peak plasma levels lower than those shown to be effective for subcutaneous injection.

The present invention relates to ion pairs of methylnaltrexone and an amphiphilic pharmaceutically acceptable excipient, methods for forming such ion pairs, methods for selecting such ion pairs, use of such ion pairs, compositions including such ion pairs, solid oral formulations of methylnaltrexone and an amphiphilic pharmaceutically acceptable excipient, including formulations containing a rapid-acting disintegrant (e.g., effervescent or carbon dioxide-producing disintegrant), as well as methods of using such compositions and formulations thereof.

In one aspect, the present invention provides a salt of methylnaltrexone of the formula:

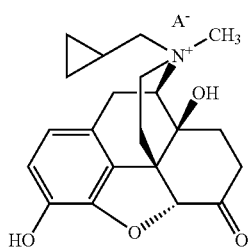

wherein methylnaltrexone is the cation of the salt, and A⁻ is an anion of an amphiphilic pharmaceutically acceptable excipient. In certain embodiments, the methylnaltrexone is (R)—N-methylnaltrexone as shown in the formula above. The amphiphilic pharmaceutically acceptable excipient is acidic. In certain embodiments, the amphiphilic pharmaceutically acceptable excipient has a $pK_a$ of about 3 or less. For example, the amphiphilic pharmaceutically acceptable excipient may include a sulfate, sulfonate, nitrate, nitrite, phosphate, or phosphonate moiety. In one embodiment, the pharmaceutically acceptable excipient comprises an (—$OSO_3^-$) group. Without wishing to be bound by a particular theory, such chemical functional groups with $pK_a$ values at or below about 3 allow for the ion pair to remain bound together at the acidic pH found in the stomach. This is because the conjugate base of the excipient remains deprotonated and negatively charged, and methylnaltrexone is quaternary amine that is positively charged. The pharmaceutically acceptable excipient also includes a hydrophobic portion. In some embodiments, the hydrophobic portion is a branched or unbranched, saturated or unsaturated, cyclic or acyclic $C_{4-30}$ aliphatic chain, which may be optionally substituted. In some embodiments the pharmaceutically acceptable excipient is, for example, a saturated or unsaturated, branched or unbranched, cyclic or acyclic $C_{4-30}$ aliphatic group that is optionally substituted. In some embodiments it is a saturated, unbranched, acyclic, unsubstituted $C_{4-30}$ alkyl group. In some embodiments, it is a saturated, unbranched, acyclic, unsubstituted $C_{7-15}$ alkyl group. In some embodiments it is a $C_{12}$ n-alkyl group. In some embodiments, it is dodecyl (lauryl) sulfate. Without wishing to be bound by any theory, it is believed that the aliphatic chain makes the excipients amphiphilic and surface active in nature, which helps transport of the ion pair through the unstirred diffusion layer lining the inner surface of the GI tract, thus increasing availability of methylnaltrexone to the GI membrane for local effects on receptor sites and/or absorption across lipophilic barriers such as the lining of the GI tract, e.g., the stomach and upper duodenum. In certain embodiments, the methylnaltrexone ion pair is a salt that is solid at room temperature.

According to another aspect of the invention, a composition is provided. The composition is the salt or ion pair described above. The salt or ion pair may comprise at least 2%, at least 5%, at least 10%, at least 20%, at least 30%, at least 50%, at least 75%, at least 90%, at least 95% or at least 99% of the methylnaltrexone in the composition. In some embodiments, the composition is a pharmaceutical composition.

In another aspect of the invention, a composition for oral administration is provided. The composition includes methylnaltrexone and an amphiphilic pharmaceutically acceptable excipient that form an ion pair or salt with methylnaltrexone when dissolved in solution, thereby increasing the octanol/water partition coefficient of methylnaltrexone. When the composition is dissolved in an aqueous solution, the methylnaltrexone has an apparent octanol/water partition coefficient of at least 0.25 in acidic conditions, and in some embodiments at a pH between 1 and 4. A pH of between 1 and 4 is used to simulate the physiological conditions of the stomach. In certain embodiments, the apparent octanol/water partition coefficient of methylnaltrexone is at least 0.5, 1.0, 5.0, 10, 20, or 30 at a pH between 1 and 4. Typically, the pharmaceutically acceptable excipient has a pKa of about 3 or less so that the conjugate base of the amphiphilic pharmaceutically acceptable excipient remains deprotonated and will be noncovalently bound to the cationic methylnaltrexone under physiological conditions found in the stomach (i.e., a solution at acidic pH).

The composition also may include a rapid-acting disintegrant, wherein the composition dissolves within about 15 minutes in the stomach. In at least one embodiment, at least 50% of the methylnaltrexone in the composition is dissolved in 15 minutes. In other embodiments, at least 75%, 80%, 85%, 90%, 95%, or even 99% of the methylnaltrexone in the composition is dissolved in 15 minutes. In any of the forgoing embodiments, the methylnaltrexone in the composition can dissolve within 10 minutes or even within 5 minutes. The dissolution of the composition in the stomach may be simulated by in vitro studies in a dissolution apparatus with paddles at 100 rpm in 900 ml 0.1N HCl at 37° C. In certain embodiments, the disintegrant is a fast-acting disintegrant. In certain embodiments, the composition has a dissolution profile substantially similar to the one depicted in FIG. 2. In some embodiments, the disintegrant is an effervescent disintegrant (i.e., one that evolves a gas). By creating gas bubbles within the composition, the composition is more readily broken down thereby releasing methylnaltrexone. Effervescent disintegrants were found to be particularly useful in aiding in the dissolution tablets containing methylnaltrexone and dodecyl sulfate. In certain embodiments, the disintegrant is an effervescent disintegrant that is capable of generating carbon dioxide when the composition is contacted with an aqueous medium. In any of the embodiments, the effervescent disintegrant can be a bicarbonate or carbonate. In any of the embodiments, the effervescent disintegrant can be sodium bicarbonate.

According to another aspect of the invention, a method of preparing a methylnaltrexone formulation is provided. The method includes combining a solid pharmaceutically acceptable salt of methylnaltrexone (that is not an ion pair of methylnaltrexone and an amphiphilic pharmaceutically acceptable excipient), such as methylnaltrexone bromide or iodide, with a solid pharmaceutically acceptable salt of the amphiphilic excipient (that is not the ion pair of methylnaltrexone and the amphiphilic pharmaceutically acceptable excipient) to form a mixture. The mixture may be wet granulated. In certain embodiments, a wet granulation of methylnaltrexone or a pharmaceutically acceptable salt thereof, an amphiphilic pharmaceutically acceptable excipient, at least one disintegrant, at least one binder, at least one chelating agent, at least one wetting agent, and optionally at least one filler is prepared and formed into a solid dosage form. In certain embodiments, a wet granulation is formed by dry blending the methylnaltrexone or a pharmaceutically acceptable salt thereof, a binder, an amphiphilic pharmaceutically acceptable excipient, and optionally a disintegrant; and granulating the dry blend with a solution of a chelating agent and/or a wetting agent to form a wet granulation. The wet granulation may be dried and milled, and the milled dried granulation blended with an additional disintegrant (e.g., sodium bicarbonate) and optionally a lubricant and/or a glidant before a solid dosage form is prepared.

In some aspects, the present invention provides compositions for oral administration comprising a salt of the cation methylnaltrexone and the anion of the amphiphilic pharmaceutically acceptable excipient (e.g., dodecyl sulfate). In some embodiments, the compositions for oral administration are tablet formulations. In some embodiments, the compositions for oral administration are capsule formulations.

In general, formulations for oral administration comprise methylnaltrexone, an amphiphilic pharmaceutically acceptable excipient as described above, and a disintegrant, and further optionally comprise one or more other components, such as, for example, binders, carriers, chelating agents, antioxidants, fillers, lubricants, wetting agents, or combinations thereof. In any of the foregoing embodiments, oral formulations are tablet formulations. In some embodiments, the present invention provides a unit dosage form comprising a formulation or composition described herein.

The present invention also provides methods of oral administration of methylnaltrexone in any context in which such administration is desirable. For example, formulations are useful for preventing, treating, or reducing the severity of side effects resulting from administration of opioids, including inhibition of intestinal motility or gastrointestinal dysfunction (e.g., constipation, GI sphincter constriction), nausea, emesis, and pruritus. The compositions and formulations are useful for administration to patients receiving acute opioid treatment (e.g., patients suffering from post operative ileus or gastrointestinal dysfunction resulting from acute opioid administration). Such formulations are also useful for administration to subjects receiving chronic opioid administration (e.g., terminally ill patients receiving opioid therapy (e.g., an AIDS patient, a cancer patient, a patient with cardiovascular disease); subjects receiving chronic opioid therapy for pain management; subjects receiving opioid therapy for maintenance of opioid withdrawal). In some embodiments, the subject is undergoing opioid therapy for chronic pain management. In other embodiments, the subject is undergoing opioid therapy for acute pain management. In certain embodiments, the pain is non-malignant pain (e.g., back pain, neuropathic pain, pain associated with fibromyalgia, osteoarthritis, etc.). In certain embodiments, the pain is chronic non-malignant pain. In certain embodiments, the pain is malignant pain. In certain embodiments, the present invention provides a method comprising the step of reducing one or more side effects of opioid therapy in a subject receiving opioid treatment comprising administering to the subject a provided tablet formulation, as described herein. In other embodiments, the present invention provides a method for reducing one of more effects of endogenous opioid activity in a subject (e.g., post partum ileus) comprising administering to the subject a formulation. In some embodiments the subject is not a methadone maintenance patient. In any of the foregoing embodiments, the subject can be fasted or fed. In one important embodiment, the subject is fasted overnight.

BRIEF DESCRIPTION OF THE DRAWINGS

FIG. 1 shows the dissolution profile of methylnaltrexone tablets and capsules in 900 ml 0.1N HCl, at 37 degrees C., 100 rpm Paddle.

FIG. 2 shows the dissolution profile of methylnaltrexone (150 mg) tablets formulated with sodium dodecyl sulfate and an effervescent disintegrant, sodium bicarbonate (as described in Example 5), at 37 degrees C., 100 rpm Paddle, analyzed using a Cary 50 spectrophotometer.

FIG. 4 includes characterization data for MNTX-heptyl sulfate.

FIG. 5 includes characterization data for MNTX-dodecyl sulfate.

FIG. 6 includes characterization data for MNTX-sodium laurate. FIG. 6B is an HPLC chromatogram for MNTX-sodium laurate. FIG. 6C is the UV spectrum of MNTX-sodium laurate.

DETAILED DESCRIPTION OF CERTAIN EMBODIMENTS OF THE INVENTION

Definitions

Figure 3:
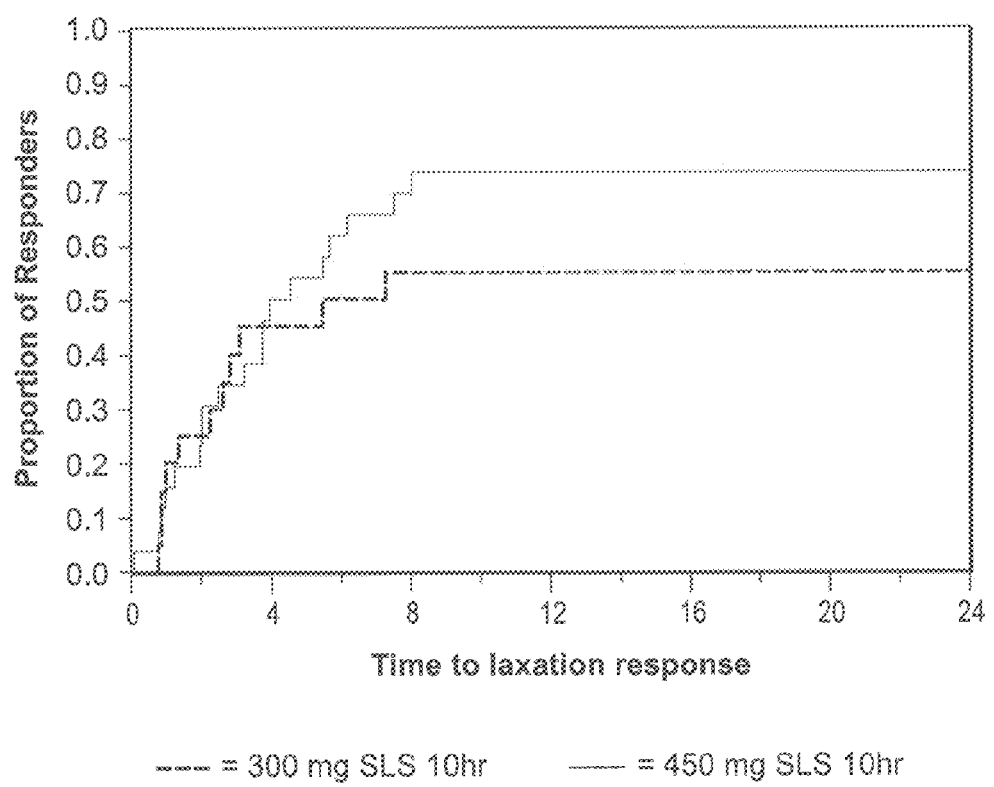
FIG. 3 shows a plot of the time and the percentage of patients having a first laxation response in patients with chronic malignant pain administered an (R)—N-methylnaltrexone bromide (300 mg or 450 mg) SDS tablet formulation after a 10 hour fast.
Figure 4A:
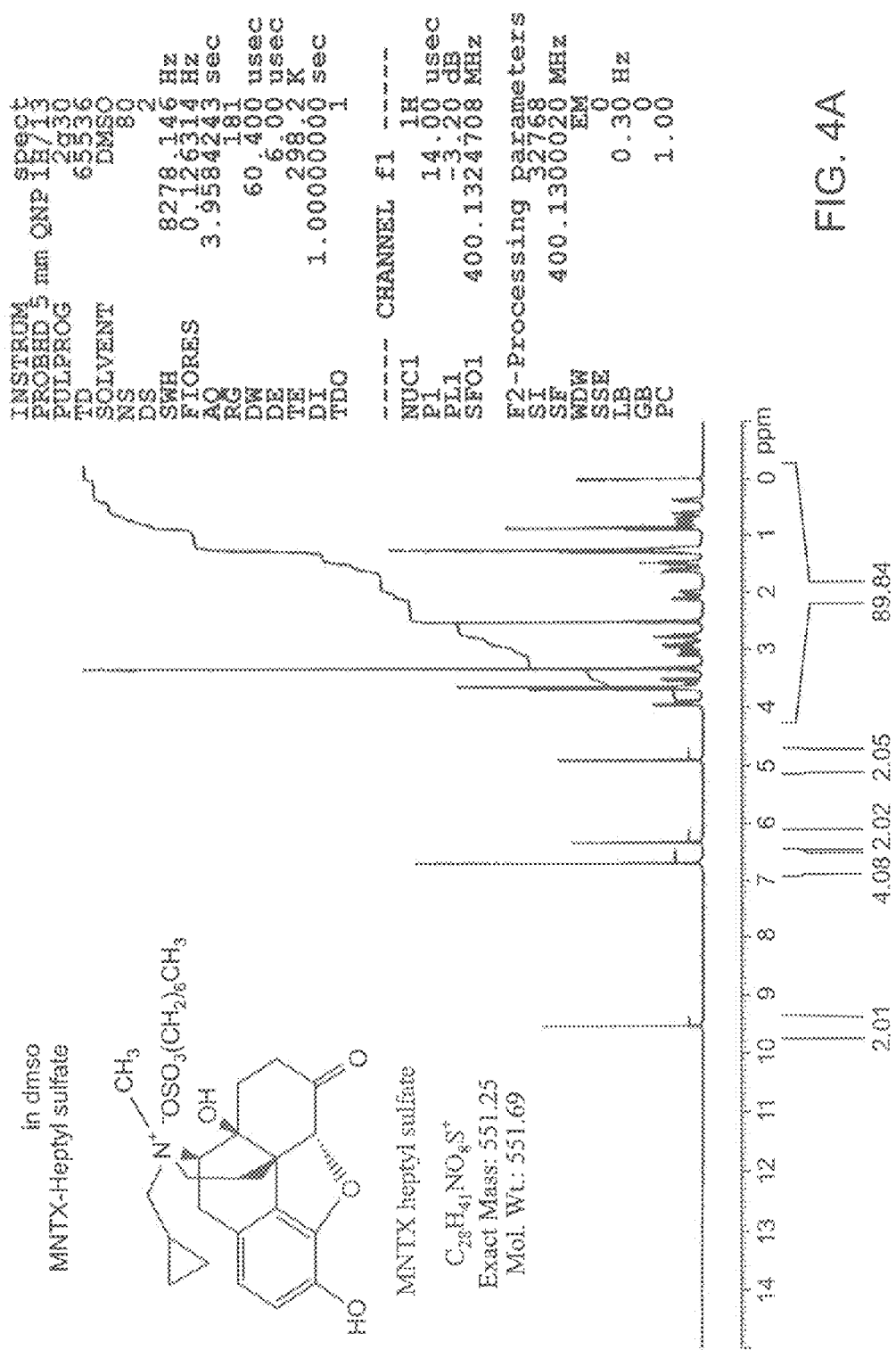
FIG. 4A is the $^1$H NMR spectrum of MNTX-heptyl sulfate.
Figures 4B, 4C:
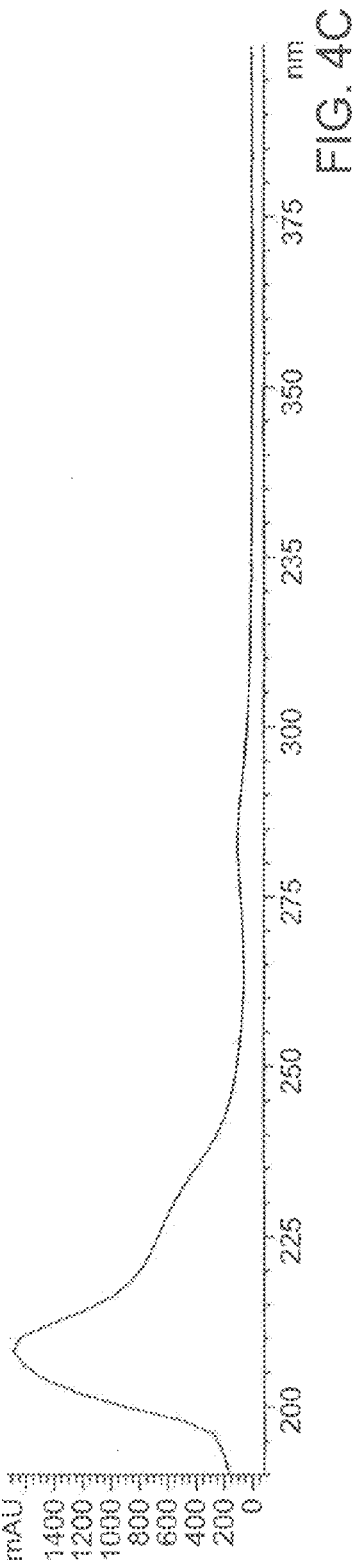
FIG. 4B is an HPLC chromatogram for MNTX-heptyl sulfate.
FIG. 4C is the UV spectrum of MNTX-heptyl sulfate.
Figure 5A:
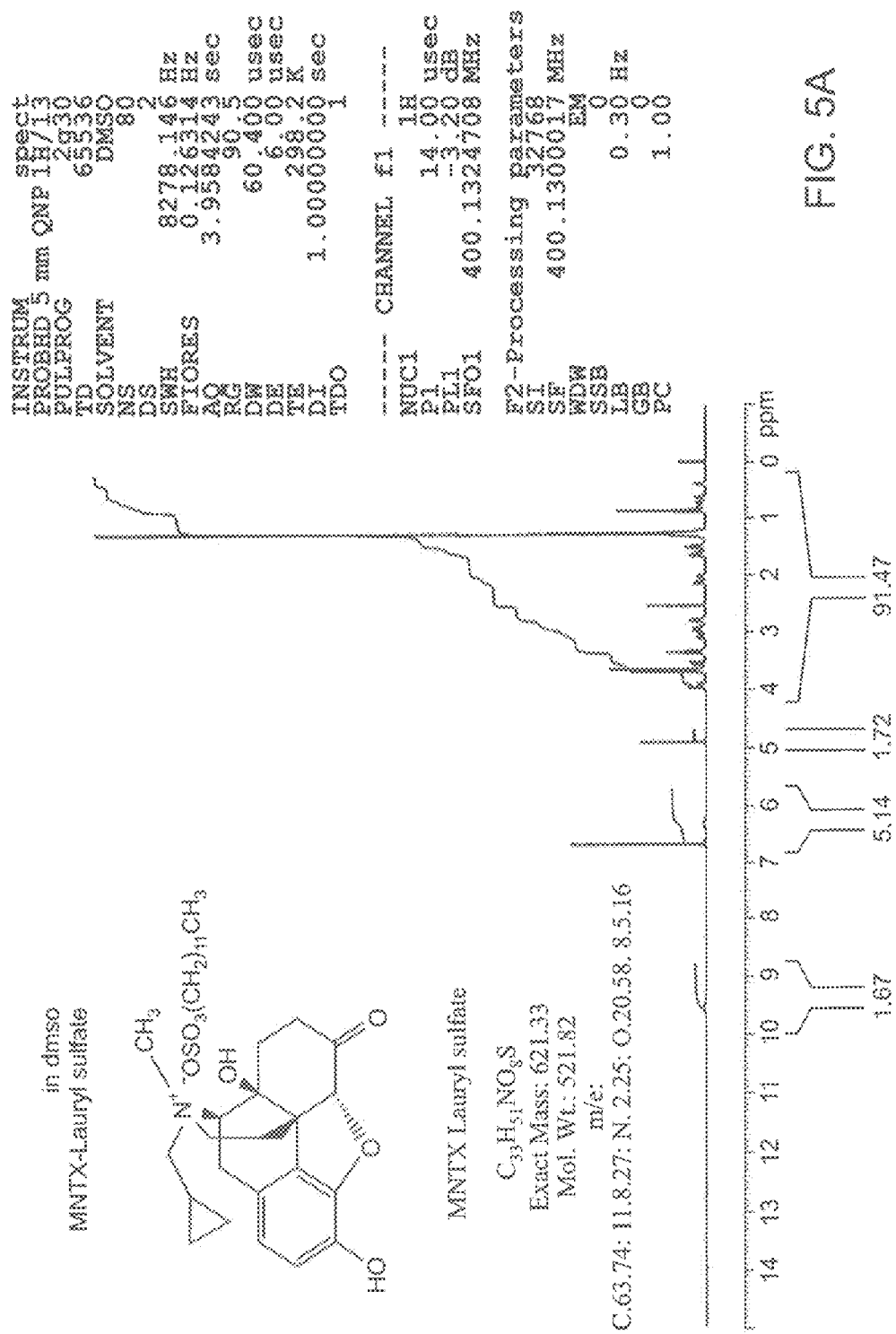
FIG. 5A is the $^1$H NMR spectrum of MNTX-dodecyl sulfate.
Figure 5B:
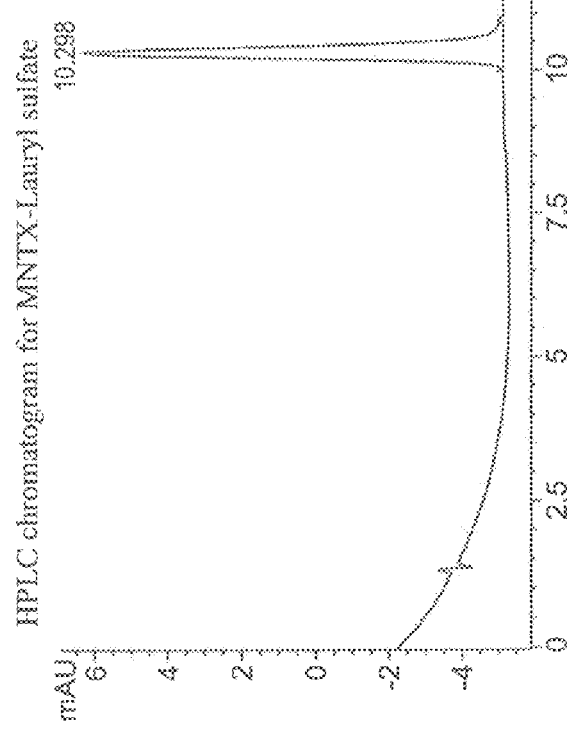
FIG. 5B is an HPLC chromatogram for MNTX-dodecyl sulfate.
Figure 5C:
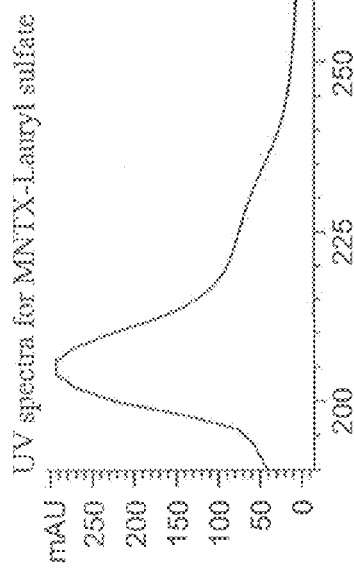
FIG. 5C is the UV spectrum of MNTX-dodecyl sulfate.
Figure 6A:
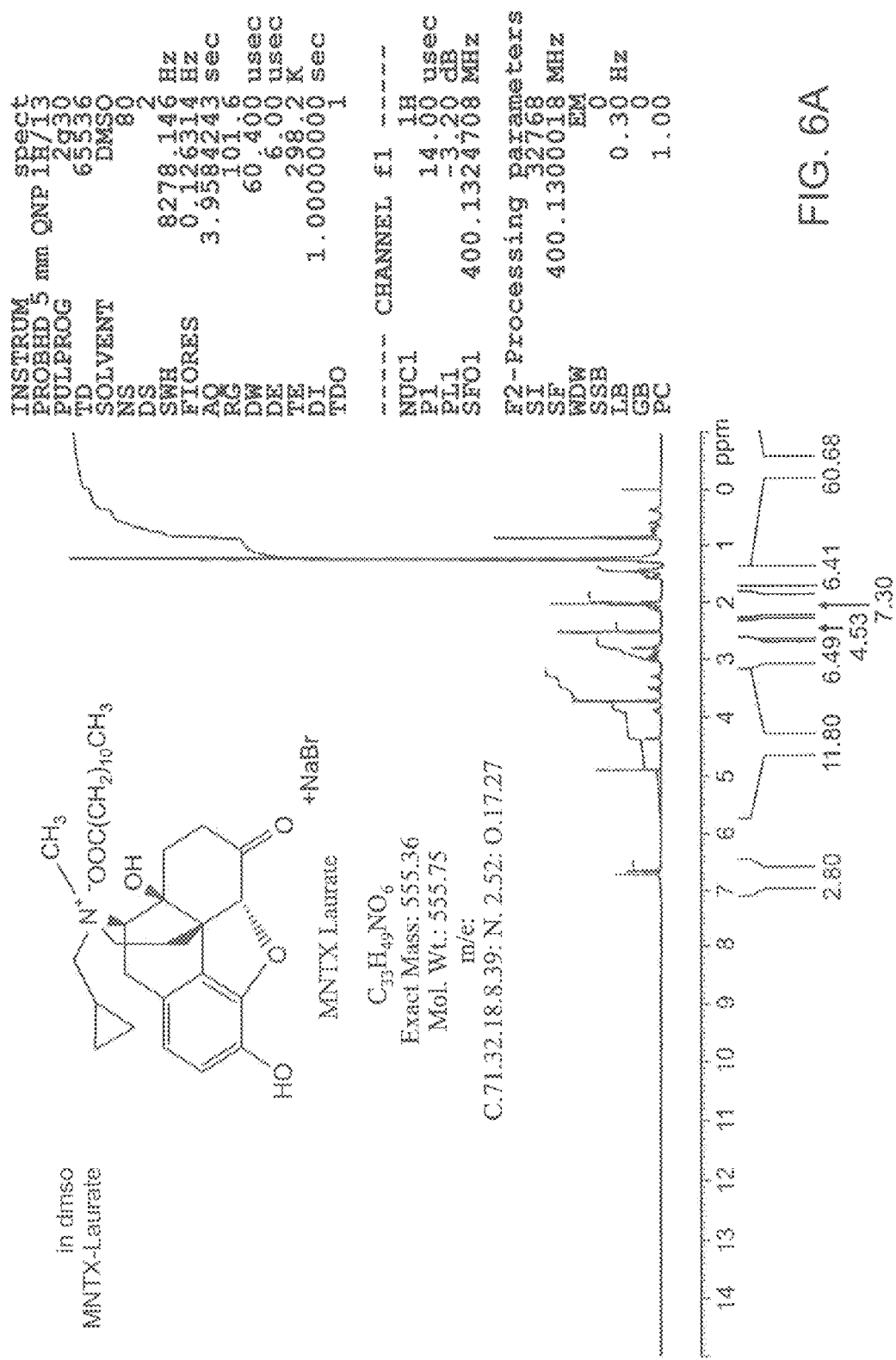
FIG. 6A is the $^1$H NMR spectrum of MNTX-sodium laurate.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched, and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-30 aliphatic carbon atoms. In certain embodiments, the alkyl, alkenyl, and alkynyl groups employed in the invention contain 10-30 aliphatic carbon atoms. In certain embodiments, the alkyl, alkenyl, and alkynyl groups employed in the invention contain 5-25 aliphatic carbon atoms. In certain embodiments, the alkyl, alkenyl, and alkynyl groups employed in the invention contain 5-20 aliphatic carbon atoms. In certain embodiments, the alkyl, alkenyl, and alkynyl groups employed in the invention contain 10-20 aliphatic carbon atoms. In certain embodiments, the alkyl, alkenyl, and alkynyl groups employed in the invention contain 15-25 aliphatic carbon atoms. In certain other embodiments, the alkyl, alkenyl, and alkynyl groups employed in the invention contain 1-10 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl, heptyl, octyl (capryl), nonyl, decyl (capric), undecyl, dodecyl (lauryl), tridecyl, tetradecyl, hexadecyl (cetyl), heptadecyl, octadecyl (stearyl), eicosyl (arachidyl), docosyl, tetracosyl, hexacosyl, octacosyl, triacontyl moieties and the like, which again, may bear one or more substituents.

Some examples of substituents of the above-described aliphatic moieties include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; and —N$_x$(CO)R$_x$; wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "amphiphilic" as used herein to describe a molecule refers to the molecule's dual hydrophobic and hydrophilic properties. Typically, amphiphilic molecules have a polar, water soluble group (e.g., a phosphate, carboxylic acid, sulfate) attached to a nonpolar, water-insoluble group (e.g., a hydrocarbon). The term amphiphilic is synonymous with amphipathic. Examples of amphiphilic molecules include sodium dodecyl (lauryl) sulfate, fatty acids, phospholipids, and bile acids. Amphiphilic molecules may be uncharged, cationic, or anionic.

As used herein, the term "dissolution rate" refers to the amount of time it takes for an active ingredient or composition thereof (e.g., a salt methylnaltrexone) to dissolve in a solvent. The dissolution rate may depend on a variety of factors including mixing, temperature, pH, solvent, particle size, etc. The dissolution rate of a drug or composition thereof affects the bioavailability of the drug. In certain circumstances, dissolution rate is used to determine drug availability from solid dosage forms.

As used herein, an "effective amount" of a compound or pharmaceutically acceptable composition or formulation can achieve a desired therapeutic and/or prophylactic effect. In some embodiments, an "effective amount" is at least a minimal amount of a compound, or formulation or composition containing a compound, which is sufficient for treating one or more symptoms of a disorder or condition associated with modulation of peripheral μ opioid receptors, such as side effects associated with opioid analgesic therapy (e.g., gastrointestinal dysfunction (e.g., dysmotility constipation, etc.), nausea, emesis, etc.). In certain embodiments, an "effective amount" of a compound, composition, or formulation containing a compound, is sufficient for treating symptoms associated with, a disease associated with aberrant endogenous peripheral opioid or μ opioid receptor activity (e.g., idiopathic constipation, ileus, etc.). In some embodiments, the term "effective amount," as used in connection with an amount of methylnaltrexone or salt of methylnaltrexone, means an amount of methylnaltrexone or salt of methylnaltrexone sufficient to achieve laxation in a patient.

The term "effervescent disintegrant," as used herein, refers to a material that causes effervescence resulting in quick disintegration of the dosage form following contact with aqueous medium. Typically the effervescent disintegrant is a base (e.g., carbonate) which reacts with an acid (e.g., HCl in the stomach) to form carbon dioxide. Therefore, such effervescent disintegrants include carbon dioxide producing disintegrants. Carbonate sources include, but are not limited to, carbonate and bicarbonate salts such as sodium bicarbonate, sodium carbonate, potassium bicarbonate, potassium carbonate, magnesium carbonate, sodium sesquicarbonate, sodium glycine carbonate, L-lysine carbonate, arginine carbonate, and calcium carbonate. Effervescent disintegrants are known in the art for achieving fast-disintegrating dosage forms.

As used herein, the term "liphophilicity" refers to a compound's ability to associate with or dissolve in a fat, lipid, oil, or non-polar solvent. Lipophilicity and hydrophobicity may be used to describe the same tendency of a molecule to dissolve in fats, oils, lipids, and non-polar solvents.

As used herein the term "non-functional coating" is a coating that does not significantly affect release characteristics of a therapeutically active compound or compounds from a formulation when administered. Examples of a non-functional coat include a seal coat (e.g., hydroxypropyl cellulose, hypromellose or polyvinyl alcohol). In certain embodiments, a non-functional coating is a polish coat or seal coat.

As used herein the term "non-malignant pain" refers to "non-cancer pain."

The term "apparent partition coefficient," as used herein, refers to the ratio of concentrations of a compound in any form in the two phases of a mixture of two immiscible solvents at equilibrium. In certain embodiments, the two immiscible solvents are octanol and water. The apparent partition coefficient may be determined under various conditions, for example, temperature, pH, concentration, etc. Apparent partition coefficients have been found useful in estimating the distribution of compounds in the body. Higher apparent partition coefficients denote a more hydrophobic (more lipophilic) compound, while lower apparent partition coefficients denote a hydrophilic compound. The apparent partition coefficient of a compound may be determined by procedures known in the art, for example, in the U.S. Pharmacopeia. The apparent partition coefficient may be determined by the procedure used to determine the apparent partition coefficients of methylnaltrexone dodecyl sulfate and methylnaltrexone heptyl sulfate in the Examples.

The term "subject", as used herein, means a mammal and includes human and animal subjects, such as domesticated animals (e.g., horses, dogs, cats, etc.) and experimental animals (e.g., mice, rats, dogs, chimpanzees, apes, etc.).

The terms "suffer" or "suffering" as used herein refers to one or more conditions that a patient has been diagnosed with, or is suspected to have.

The term "spheroid", as used herein, has its art understood meaning of a substantially spherical particulate. In many embodiments, spheroids prepared or utilized according to the present invention have a size within the range of about 1-1500 microns. In some embodiments, such spheroids have a size within the range of about 20-1500 microns. In some embodiments, such spheroids have a size within the range of about 20-1000 microns. In some embodiments, such spheroids have a size within the range of about 20-500 microns. In some embodiments, such spheroids have a size within the range of about 20-300 microns. In certain embodiments, the spheroids have a size range wherein at least 80% of the spheroids fall within the range of about 20-325 microns. In some embodiments, the spheroids have a size range wherein at least 50% of the spheroids fall within the range of about 45-120 microns.

The terms "treat" or "treating," as used herein, refers to partially or completely alleviating, inhibiting, delaying onset of, reducing the incidence of, ameliorating and/or relieving a disorder or condition, or one or more symptoms of the disorder, disease or condition.

"Therapeutically active agent" or "active agent" refers to a substance, including a biologically active substance, that is useful for therapy (e.g., human therapy, veterinary therapy), including prophylactic and therapeutic treatment. Therapeutically active agents include organic molecules that are drug compounds, peptides, proteins, carbohydrates, monosaccharides, oligosaccharides, polysaccharides, nucleoprotein, mucoprotein, lipoprotein, synthetic polypeptide or protein, small molecules linked to a protein, glycoprotein, steroid, nucleic acid, DNA, RNA, nucleotide, nucleoside, oligonucleotides, antisense oligonucleotides, lipid, hormone, and vitamin. Therapeutically active agents include any substance used as a medicine for treatment, prevention, delay, reduction or amelioration of a disease, condition, or disorder. Among therapeutically active agents useful in the formulations of the present invention are opioid receptor antagonist compounds, opioid analgesic compounds, and the like. Further detailed description of compounds useful as therapeutically active agents is provided below. A therapeutically active agent includes a compound that increases the effect or effectiveness of a second compound, for example, by enhancing potency or reducing adverse effects of a second compound.

The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism will depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

The term "$pK_a$," as used herein, refers to the $-\log_{10}K_a$, wherein $K_a$ is the acid dissociation constant. $pK_a$ measures the strength of an acid in solution on a logarithmic scale. The acid dissociation constant $K_a$ is the equilibrium constant for the dissociation of a compound into a proton and its conjugate base, symbolically written as:

Compositions and Formulations of Methylnaltrexone

As used herein, methylnaltrexone refers to (R)—N-methylnaltrexone. (R)—N-methylnaltrexone, a peripherally acting μ opioid receptor antagonist, has been studied and used to treat bowel dysfunction in patients being administered opioids. Surprisingly, enterically coated preparations of methylnaltrexone do not consistently demonstrate a substantial effect in treating opioid-induced constipation. Contrary to the suggestions of the prior art concerning oral methylnaltrexone, local concentrations of methylnaltrexone in the intestinal tract remote from the stomach, are not effective to induce laxation and treat constipation.

In certain embodiments, the present invention provides a composition comprising methylnaltrexone and a pharmaceutically acceptable excipient, wherein the composition in solution yields an octanol/water apparent partition coefficient for methylnaltrexone of at least 0.25 under acidic conditions, in certain embodiments at a pH between 1 and 4. In some embodiments, such compositions are formulated for oral administration. In some embodiments, a composition for oral administration is formulated into a tablet. Methylnatrexone for use in such compositions and formulations may be in any of a variety of forms. For example, forms of methylnaltrexone suitable for use in the inventive compositions and formulations include pharmaceutically acceptable salts, prodrugs, polymorphs (i.e., crystal forms), co-crystals, hydrates, solvates, and the like. Any form of methylnaltrexone may be used in the compositions or formulations, but the form should allow for ion pairing with the amphiphilic pharmaceutically acceptable excipient.

In certain embodiments, the compositions, and formulations thereof, comprise a salt of formula I:

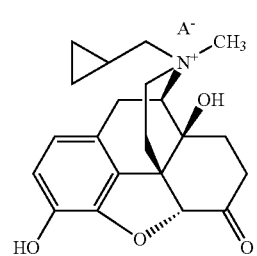

I wherein $A^-$ is a suitable anion. In certain embodiments, $A^-$ is the anion of a Brønsted acid. Exemplary Brønsted acids include hydrogen halides, carboxylic acids, sulfonic acids, sulfuric acid, and phosphoric acid. In certain embodiments, $A^-$ is chloride, bromide, iodide, fluoride, sulfate, bisulfate, tartrate, nitrate, citrate, bitartrate, carbonate, phosphate, malate, maleate, fumarate sulfonate, methylsulfonate, formate, carboxylate, sulfate, methylsulfate or succinate salt. In certain embodiments, $A^-$ is trifluoroacetate. In certain embodiments, $A^-$ is bromide. In certain embodiments, $A^-$ is an anion of an amphiphilic pharmaceutically acceptable excipient. In certain embodiments, $A^-$ is an acidic amphiphilic pharmaceutically acceptable excipient. In certain embodiments, the pharmaceutically acceptable excipient has a $pK_a$ of about 3 or less. In certain embodiments, the pharmaceutically acceptable excipient has a $pK_a$ of about 2 or less. In certain embodiments, the pharmaceutically acceptable excipient has a $pK_a$ between about 1 and about 2. In certain embodiments, the pharmaceutically acceptable excipient has a $pK_a$ of about 1 or less. In certain embodiments, the anion of the pharmaceutically acceptable excipient include a sulfate, sulfonate, phosphate, phosphonate, nitrate, or nitrite moiety. In certain embodiments, the anion of the pharmaceutically acceptable excipient includes a sulfate ($-OSO_3^-$) group. In certain embodiments, the anion is butyl sulfate, pentyl sulfate, hexyl sulfate, heptyl sulfate, octyl sulfate, nonyl sulfate, decyl sulfate, undecyl sulfate, dodecyl sulfate, tridecyl sulphate, tetradecyl sulfate, pentadecyl sulfate, hexadecyl sulfate, heptadecyl sulfate, octadecyl sulfate, eicosyl sulfate, docosyl sulfate, tetracosyl sulfate, hexacosyl sulfate, octacosyl sulfate, and triacontyl sulphate. In certain embodiments, the methylnaltrexone in the composition or formulation may have multiple anions (e.g., bromide and dodecyl (lauryl) sulfate) associate with it.

In some embodiments, the compositions, and formulations thereof, comprise (R)—N-methylnaltrexone bromide. (R)—N-methylnaltrexone bromide, which is also known as "MNTX" and is described in international PCT patent application publication number, WO2006/12789, which is incorporated herein by reference. The chemical name for (R)—N-methylnaltrexone bromide is (R)—N-(cyclopropylmethyl) noroxymorphone methobromide. (R)—N-methylnaltrexone bromide has the molecular formula $C_{21}H_{26}NO_4Br$ and a molecular weight of 436.36 g/mol. (R)—N-methylnaltrexone bromide has the following structure:

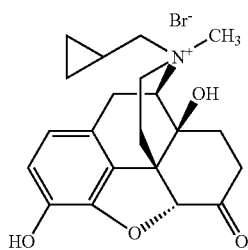

(R)—N-methylnaltrexone bromide where the compound is in the (R) configuration with respect to the quaternary nitrogen. In certain embodiments of the present invention, at least about 99.6%, 99.7%, 99.8%, 99.85%, 99.9%, or 99.95% of the compound is in the (R) configuration with respect to nitrogen. Methods for determining the amount of (R)—N-methylnaltrexone bromide, present in a sample as compared to the amount of (S)—N-methylnaltrexone bromide present in that same sample, are described in detail in WO2006/127899, which is incorporated herein by reference. In other embodiments, the methylnaltrexone contains 0.15%, 0.10%, or less (S)—N-methylnaltrexone bromide.

In some embodiments, a composition, or formulation thereof, comprises from about 7% to about 75%, about 25% to about 55%, about 40%, or to about 50% (R)—N-methylnaltrexone cation, based upon total weight of the formulation. In certain embodiments, a provided composition, or formulation thereof, comprises from about 7%, about 8%, about 10%, about 20%, about 30%, about 40%, about 50%, about 60%, about 70%, or about 75% (R)—N-methylnaltrexone cation, based upon the total weight of the given composition or formulation. It will be understood that the (R)—N-methylnaltrexone cation and the anion of the amphiphilic pharmaceutically acceptable excipient may exist in the composition as an ion pair or may exist as separate salts paired with other counter ions such as bromide and sodium, or mixtures thereof.

In some embodiments, a composition, or formulation thereof, comprises from about 7% to about 75%, about 25% to about 55%, about 40%, or to about 50% (R)—N-methylnaltrexone cation and dodecyl sulfate anion, based upon the total weight of the composition or formulation. In certain embodiments, a composition, or formulation thereof, comprises from about 7%, about 8%, about 10%, about 20%, about 30%, about 40%, about 50%, about 60%, about 70%, or about 75% (R)—N-methylnaltrexone cation and dodecyl sulfate anion, based upon total weight of the composition or formulation.

In certain embodiments, the present invention provides a composition comprising methylnaltrexone and an amphiphilic pharmaceutically acceptable excipient. The amphiphlic pharmaceutically acceptable excipient increases the lipophilicity of the composition thereby allowing for increased transport through the unstirred diffusion layer in the GI tract, resulting in increased permeation through biological membranes. In certain embodiments, the excipient increases the lipophilicity of the drug. In certain embodiments, the excipient is a surfactant. In some embodiments, the excipient is an anionic surfactant. In certain embodiments, the excipient is an anionic surfactant that forms an ion pair or salt with positively charged methylnaltrexone. Such anionic surfactants are known in the art and are typically characterized by having a lipophilic end and an anionic portion. Exemplary excipients useful in the present invention include aliphatic sulfates (e.g., sodium dodecyl (lauryl) sulfate), aliphatic phosphates, fatty acids, and salts and derivatives thereof.

As a measure of lipophilicity of the resulting ion pair, a solution of the composition yields an apparent octanol/water partition coefficient for methylnaltrexone of at least 0.25 at a pH between 1 and 4. The apparent octanol/water partition coefficient as used herein is determined at room temperature at a concentration of approximately 0.5 mg/mL. Exemplary methods for the determination of apparent octanol/water partition coefficient of methylnaltrexone salts are described in the Examples below.

Particularly useful amphiphilic pharmaceutically acceptable excipient includes those that increase the oral absorption of methylnaltrexone. In certain embodiments, the excipient increases the absorption of methylnaltrexone in the stomach. In certain embodiments, the excipient increases the ability of methylnaltrexone to cross lipophilic barriers. In certain embodiments, the excipient increases the lipophilicity of methylnaltrexone by forming an ion pair with cationic methylnaltrexone. Ion pairing increases the partitioning of methylnaltrexone into an organic phase such as a lipid bilayer. In certain embodiments, the excipient forms an ion pair with methylnaltrexone such that when the composition is in solution, the methylnaltrexone has an apparent octanol/water partition coefficient of at least 0.25 at a pH between 1 and 4. In certain embodiments, the apparent octanol/water partition coefficient is at least 0.5 at a pH between 1 and 4. In certain embodiments, the apparent octanol/water partition coefficient is at least 0.75 at a pH between 1 and 4. In certain embodiments, the apparent octanol/water partition coefficient is at least 1.0 at a pH between 1 and 4. In certain embodiments, the apparent octanol/water partition coefficient is at least 10 at a pH between 1 and 4. In certain embodiments, the apparent octanol/water partition coefficient is at least 15 at a pH between 1 and 4. In certain embodiments, the apparent octanol/water partition coefficient is at least 20 at a pH between 1 and 4. In certain embodiments, the apparent octanol/water partition coefficient is at least 25 at a pH between 1 and 4. In certain embodiments, the apparent octanol/water partition coefficient is at least 30 at a pH between 1 and 4.

As used herein, the term "aliphatic sulfate" refers to a compound having a sulfate moiety at one end and an aliphatic tail, which is straight or branched, and saturated or unsaturated. The aliphatic tail may be substituted and may also include cyclic groups. In some embodiments, the aliphatic tail is a $C_4$ to $C_{30}$ aliphatic group. In certain embodiments, the aliphatic tail is a $C_7$ to $C_{20}$ aliphatic group. In certain embodiments, the aliphatic tail is a $C_{10}$ to $C_{20}$ aliphatic group. In certain embodiments, the aliphatic tail is a $C_{10}$, $C_{11}$, $C_{12}$, $C_{13}$, $C_{14}$, or $C_{15}$ aliphatic group. In certain embodiments, the aliphatic group is an n-alkyl group, which is saturated, not branched, and not substituted. In certain embodiments, the aliphatic group is $C_7$-$C_{20}$ n-alkyl. In certain embodiments, the aliphatic group is $C_{10}$-$C_{15}$ n-alkyl.

In certain embodiments, the amphiphilic pharmaceutically acceptable excipient is a compound of formula:

$$R^1\text{—}OSO_2OH$$

or a salt thereof, wherein $R^1$ is a $C_{4-30}$ aliphatic group that is saturated or unsaturated, unbranched or branched, and cyclic or acyclic, and the aliphatic group is optionally substituted with one or more halogen or hydroxyl groups. In certain embodiments, each $R^1$ is a $C_{4-10}$ aliphatic group. In certain embodiments, each $R^1$ is a $C_{10-15}$ aliphatic group. In certain embodiments, each $R^1$ is a $C_{15-20}$ aliphatic group. In certain embodiments, each $R^1$ is a $C_{20-30}$ aliphatic group. In certain embodiments, $R^1$ is unsaturated. In certain embodiments, $R^1$ is saturated. In certain embodiments, $R^1$ is unbranched. In certain embodiments, $R^1$ is branched. In certain embodiments, R1 is substituted. In certain embodiments, $R^1$ is unsubstituted. In certain embodiments, $R^1$ is saturated, unbranched, and unsubstituted. In certain embodiments, $R^1$ is $C_{4-30}$ n-alkyl. In certain embodiments, $R^1$ is $C_{5-15}$ n-alkyl. In certain embodiments, $R^1$ is $C_{5-10}$ n-alkyl. In certain embodiments, $R^1$ is $C_{10-15}$ n-alkyl. In certain embodiments, $R^1$ is $C_6$ n-alkyl. In certain embodiments, $R^1$ is $C_7$ n-alkyl. In certain embodiments, $R^1$ is $C_8$ n-alkyl. In certain embodiments, $R^1$ is $C_9$ n-alkyl. In certain embodiments, $R^1$ is $C_{10}$ n-alkyl. In certain embodiments, $R^1$ is $C_{11}$ n-alkyl. In certain embodiments, $R^1$ is $C_{12}$ n-alkyl. In certain embodiments, $R^1$ is $C_{13}$ n-alkyl. In certain embodiments, $R^1$ is $C_{14}$ n-alkyl. In certain embodiments, $R^1$ is $C_{15}$ n-alkyl. In certain embodiments, the excipient is a sodium salt form.

In certain embodiments, the amphiphilic pharmaceutically acceptable excipient is a compound of formula:

$R^1$—$SO_2OH$ or a salt thereof, wherein $R^1$ is a $C_{4-30}$ aliphatic group that is saturated or unsaturated, unbranched or branched, and cyclic or acyclic, and the aliphatic group is optionally substituted with one or more halogen or hydroxyl groups. In certain embodiments, each $R^1$ is a $C_{4-10}$ aliphatic group. In certain embodiments, each $R^1$ is a $C_{10-15}$ aliphatic group. In certain embodiments, each $R^1$ is a $C_{15-20}$ aliphatic group. In certain embodiments, each $R^1$ is a $C_{20-30}$ aliphatic group. In certain embodiments, $R^1$ is unsaturated. In certain embodiments, $R^1$ is saturated. In certain embodiments, $R^1$ is unbranched. In certain embodiments, $R^1$ is branched. In certain embodiments, $R^1$ is substituted. In certain embodiments, $R^1$ is unsubstituted. In certain embodiments, $R^1$ is saturated, unbranched, and unsubstituted. In certain embodiments, $R^1$ is $C_{4-30}$ n-alkyl. In certain embodiments, $R^1$ is $C_{5-15}$ n-alkyl. In certain embodiments, $R^1$ is $C_{5-10}$ n-alkyl. In certain embodiments, $R^1$ is $C_{10-15}$ n-alkyl. In certain embodiments, $R^1$ is $C_6$ n-alkyl. In certain embodiments, $R^1$ is $C_7$ n-alkyl. In certain embodiments, $R^1$ is $C_8$ n-alkyl. In certain embodiments, $R^1$ is $C_9$ n-alkyl. In certain embodiments, $R^1$ is $C_{10}$ n-alkyl. In certain embodiments, $R^1$ is $C_{11}$ n-alkyl. In certain embodiments, $R^1$ is $C_{12}$ n-alkyl. In certain embodiments, $R^1$ is $C_{13}$ n-alkyl. In certain embodiments, $R^1$ is $C_{14}$ n-alkyl. In certain embodiments, $R^1$ is $C_{15}$ n-alkyl. In certain embodiments, the excipient is a sodium salt form.

In certain embodiments, the amphiphilic pharmaceutically acceptable excipient is a compound of formula:

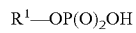
$R^1$—$P(O)_2OH$ or a salt thereof, wherein $R^1$ is a $C_{4-30}$ aliphatic group that is saturated or unsaturated, unbranched or branched, and cyclic or acyclic, and the aliphatic group is optionally substituted with one or more halogen or hydroxyl groups. In certain embodiments, each $R^1$ is a $C_{4-10}$ aliphatic group. In certain embodiments, each $R^1$ is a $C_{10-15}$ aliphatic group. In certain embodiments, each $R^1$ is a $C_{15-20}$ aliphatic group. In certain embodiments, each $R^1$ is a $C_{20-30}$ aliphatic group. In certain embodiments, $R^1$ is unsaturated. In certain embodiments, $R^1$ is saturated. In certain embodiments, $R^1$ is unbranched. In certain embodiments, $R^1$ is branched. In certain embodiments, R1 is substituted. In certain embodiments, $R^1$ is unsubstituted. In certain embodiments, $R^1$ is saturated, unbranched, and unsubstituted. In certain embodiments, $R^1$ is $C_{4-30}$ n-alkyl. In certain embodiments, $R^1$ is $C_{5-15}$ n-alkyl. In certain embodiments, $R^1$ is $C_{5-10}$ n-alkyl. In certain embodiments, $R^1$ is $C_{10-15}$ n-alkyl. In certain embodiments, $R^1$ is $C_6$ n-alkyl. In certain embodiments, $R^1$ is $C_7$ n-alkyl. In certain embodiments, $R^1$ is $C_8$ n-alkyl. In certain embodiments, $R^1$ is $C_9$ n-alkyl. In certain embodiments, $R^1$ is $C_{10}$ n-alkyl. In certain embodiments, $R^1$ is $C_{11}$ n-alkyl. In certain embodiments, $R^1$ is $C_{12}$ n-alkyl. In certain embodiments, $R^1$ is $C_{13}$ n-alkyl. In certain embodiments, $R^1$ is $C_{14}$ n-alkyl. In certain embodiments, $R^1$ is $C_{15}$ n-alkyl. In certain embodiments, the excipient is a sodium salt form.

In certain embodiments, the amphiphilic pharmaceutically acceptable excipient is a compound of formula:

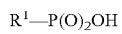
$R^1$—$OP(O)_2OH$ or a salt thereof, wherein $R^1$ is a $C_{4-30}$ aliphatic group that is saturated or unsaturated, unbranched or branched, and cyclic or acyclic, and the aliphatic group is optionally substituted with one or more halogen or hydroxyl groups. In certain embodiments, each $R^1$ is a $C_{4-10}$ aliphatic group. In certain embodiments, each $R^1$ is a $C_{10-15}$ aliphatic group. In certain embodiments, each $R^1$ is a $C_{15-20}$ aliphatic group. In certain embodiments, each $R^1$ is a $C_{20-30}$ aliphatic group. In certain embodiments, $R^1$ is unsaturated. In certain embodiments, $R^1$ is saturated. In certain embodiments, $R^1$ is unbranched. In certain embodiments, $R^1$ is branched. In certain embodiments, R1 is substituted. In certain embodiments, $R^1$ is unsubstituted. In certain embodiments, $R^1$ is saturated, unbranched, and unsubstituted. In certain embodiments, $R^1$ is $C_{4-30}$ n-alkyl. In certain embodiments, $R^1$ is $C_{5-15}$ n-alkyl. In certain embodiments, $R^1$ is $C_{5-10}$ n-alkyl. In certain embodiments, $R^1$ is $C_{10-15}$ n-alkyl. In certain embodiments, $R^1$ is $C_6$ n-alkyl. In certain embodiments, $R^1$ is $C_7$ n-alkyl. In certain embodiments, $R^1$ is $C_8$ n-alkyl. In certain embodiments, $R^1$ is $C_9$ n-alkyl. In certain embodiments, $R^1$ is $C_{10}$ n-alkyl. In certain embodiments, $R^1$ is $C_{11}$ n-alkyl. In certain embodiments, $R^1$ is $C_{12}$ n-alkyl. In certain embodiments, $R^1$ is $C_{13}$ n-alkyl. In certain embodiments, $R^1$ is $C_{14}$ n-alkyl. In certain embodiments, $R^1$ is $C_{15}$ n-alkyl. In certain embodiments, the excipient is a sodium salt form.

One of ordinary skill in the art will recognize that methylnaltrexone may form an ion pair or salt with an anionic amphiphilic pharmaceutically acceptable excipient. In some embodiments, the present invention provides a compound of formula II:

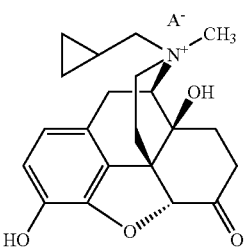

II wherein $A^-$ is an anionic amphiphilic pharmaceutically acceptable excipient.

In some aspects, methylnaltrexone may form an ion pair with any of formulae $R^1$—COOH, $R^1$—$SO_2OH$, $R^1$—$OSO_2OH$, $R^1$—$P(O)_2OH$, $R^1$—$OP(O)_2OH$, or a salt thereof, as described herein. Thus, according to another embodiment, the present invention provides a compound of any of formula III, formula IV, formula V, formula VI, or formula VII:

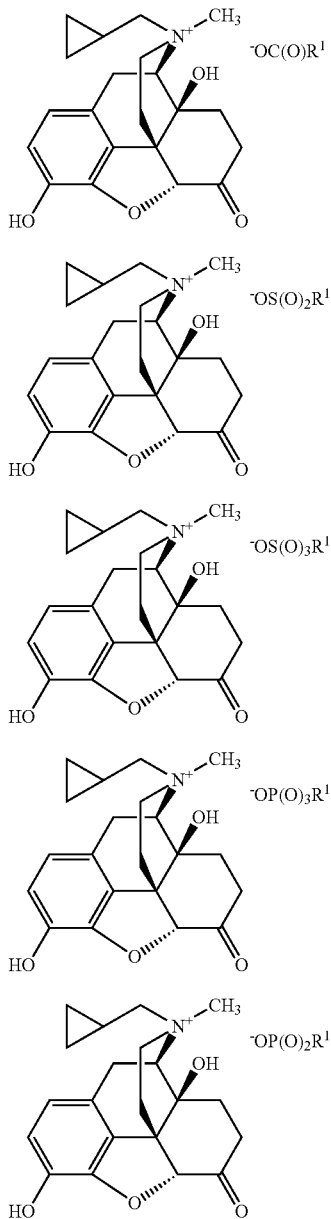

wherein $R^1$ is a $C_{4-30}$ aliphatic group that is saturated or unsaturated, unbranched or branched, and cyclic or acyclic, and the aliphatic group is optionally substituted with one or more halogen or hydroxyl groups.

In some embodiments, the amphiphilic pharmaceutically acceptable excipient is sodium dodecyl (lauryl) sulfate (also known as SDS or SLS), sodium heptyl sulfate, sodium heptyl sulfonate, perfluorooctanesulfonate (PFOS), and the like.

In some embodiments, compositions, i.e., pharmaceutical compositions comprising methylnaltrexone and sodium dodecyl (lauryl) sulfate (also known as SDS or SLS), are provided.

In some embodiments, a provided composition, or formulation thereof, comprises from about 5% to about 80% of the amphiphilic pharmaceutically acceptable excipient, based upon total weight of the composition, or formulation thereof. In certain embodiments, about 5% to about 25% of amphiphilic pharmaceutically acceptable excipient is used in the composition or formulation. In some embodiments, a provided composition, or formulation thereof, comprises about 5%, about 10%, about 15%, about 20%, about 25%, about 30%, about 35%, about 40%, about 45%, about 50%, about 55%, about 60%, about 65%, about 70%, about 75%, or about 80% of the excipient, based upon total weight of the composition, or formulation thereof.

Certain amphiphilic pharmaceutically acceptable excipients and their corresponding methylnaltrexone ion pairs are less soluble compared to methylnaltrexone bromide in an aqueous environment. In certain embodiments, therefore, the present invention provides a composition or formulation comprising methylnaltrexone, or a salt thereof, an amphiphilic pharmaceutically acceptable excipient, and a disintegrant. Incorporation of a suitable rapid-acting disintegrant into compositions and formulations facilitates the breakdown of tablets or other solid dosage forms, in particular, the rapid breakdown of tablets or other solid dosage forms in the stomach. Thus, the inclusion of rapid-acting disintegrants is desired in solid dosage forms, such as tablets, that contain active ingredient. The amount of the disintegrant will vary, depending on the nature and amount of the amphiphilic pharmaceutically acceptable excipient (and, optionally, other ingredients). Those skilled in the art will understand how to manufacture a solid dosage form which will dissolve in the stomach according to the parameters described above. There exist in vitro models, for making such determinations, such as the United States Pharmacopeia (USP) dissolution test, the USP disintegration test, etc. In some embodiments, at least 50% of the methylnaltrexone in the composition dissolves in 15 minutes. In other embodiments, at least 75%, 80%, 85%, 90%, 95%, or even 99% of the methylnaltrexone in the composition dissolves in 15 minutes. In some embodiments, the amounts of methylnaltrexone indicated above dissolve in about 10 minutes, or even about 5 minutes. As used herein by dissolve a certain percent in the stomach within a particular time period, it is meant the percent of the methylnaltrexone, as a cation or as a salt such as an ion pair, in the composition that will convert from a solid into solution when the composition is placed in 900 ml of 1N HCl at 37° C., 100 rpm Paddle.

Suitable disintegrants are known in the art and include, but are not limited to, agar, calcium carbonate, potato or tapioca starch, alginic acid, certain silicates, sodium carbonate, sodium bicarbonate, crospovidone (cross-linked PVP), sodium carboxymethyl starch (sodium starch glycolate), cross-linked sodium carboxymethyl cellulose (croscarmellose), pregelatinized starch (starch 1500), microcrystalline starch, water insoluble starch, calcium carboxymethyl cellulose, magnesium aluminum silicate (Veegum), and combinations thereof. In some embodiments, the disintegrant is crospovidone. In certain embodiments, the disintegrant is an effervescent disintegrant. Effervescent disintegrants are capable of generating carbon dioxide in an aqueous medium, particularly acidic aqueous medium such as the contents of the stomach. In certain embodiments, the disintegrant is a bicarbonate, such as sodium bicarbonate ($NaHCO_3$) or potassium bicarbonate ($KHCO_3$). In certain embodiments, the disintegrants is a carbonate. In certain embodiments, the disintegrant is sodium carbonate ($Na_2CO_3$). In certain embodiments, the disintegrant is calcium carbonate ($CaCO_3$). In certain embodiments, the composition or formulation comprises at least two disintegrants. For example, the composition or formulation may include one effervescent disintegrant and one disintegrant that is not effervescent. In certain embodiments, the compositions or formulation comprises sodium bicarbonate and crospovidone as disintegrants. In some embodiments, provided formulations comprise from about 1% to about 25%, about 1% to about 15%, about 1% to about 10%, or about 2% to about 5% disintegrant, based upon total weight of the formulation. In some embodiments, provided formulations comprise from about 1%, about 2%, about 3%, about 4%, about 5%, about 7%, about 8%, about 10%, about 12%, or about 15% disintegrant, based upon total weight of the formulation. In certain embodiments, the composition or formulation includes a material and/or coating that retards or prevents dissolution of the solid dosage form in the oral cavity. Preferably, the solid dosage form breaks down or disintegrates rapidly in the stomach, not in the oral cavity.

In some embodiments, the present invention provides a formulation of methylnatrexone which further comprises one or more additional components, such as, for example, binders, carriers, disintegrants, chelating agents, antioxidants, fillers, wetting agents, or combinations thereof. In certain embodiments, a composition is formulated into a tablet which further comprises one or more additional components, such as, for example, binders, carriers, disintegrants, chelating agents, antioxidants, fillers, wetting agents, lubricants, or combinations thereof. In some embodiments, a composition is formulated into a tablet which further comprises an antioxidant and one or more components, such as, for example, binders, carriers, chelating agents, fillers, wetting agents, or combinations thereof. In some embodiments, a composition is formulated into a tablet which further comprises a disintegrant and one or more components, such as, for example, binders, carriers, chelating agents, antioxidants, fillers, wetting agents, or combinations thereof. In some embodiments, a composition is formulated into a tablet which further comprises an antioxidant, a disintegrant, and one or more components, such as, for example, binders, carriers, chelating agents, fillers, wetting agents, or combinations thereof. Such additional components are described in detail herein, infra.

In certain embodiments, pharmaceutically acceptable formulations of the present invention are provided as tablets which comprise a composition comprising methylnaltrexone and an amphiphilic pharmaceutically acceptable excipient, and a disintegrant, and, optionally, one or more of a binder, a chelating agent, and a wetting agent. In some embodiments such tablets comprise a composition comprising methylnaltrexone and an amphiphilic pharmaceutically acceptable excipient, a binder, a chelating agent, a disintegrant, and a wetting agent. In certain embodiments such tablets comprise a composition comprising methylnaltrexone and an amphiphilic pharmaceutically acceptable excipient, an antioxidant, and one or more of a binder, a chelating agent, a disintegrant, and a wetting agent. According to some embodiments, provided formulations comprise tablets that have a non-functional coating. In some embodiments, provided formulations further comprise an antioxidant.

One skilled in the art will readily appreciate that the category under which a particular component is listed is not intended to be limiting; in some cases a particular component might appropriately fit into more than one category. Also, as will be appreciated, the same component can sometimes perform different functions, or can perform more than one function, in the context of a particular formulation, for example depending upon the amount of the ingredient and/or the presence of other ingredients and/or active compound(s).

Wetting agents are well known in the art and typically facilitate the interaction of an active agent, such as one that is hydrophobic, with water molecules in a surrounding aqueous environment. Exemplary wetting agents include poloxamer, polyoxyethylene ethers, polyoxyethylene sorbitan fatty acid esters polyoxyethylene fatty acid esters, polyethylene glycol fatty acid esters, polyoxyethylene hydrogenated castor oil, polyoxyethylene alkyl ether, polysorbates, such as polysorbate 80, cetyl alcohol, glycerol fatty acid esters (e.g., triacetin, glycerol monostearate, and the like), polyoxymethylene stearate, sodium dodecyl sulfate, sorbitan fatty acid esters, sucrose fatty acid esters, benzalkonium chloride, polyethoxylated castor oil, and docusate sodium, and the like, and combinations thereof. In some embodiments, provided tablets comprise from about 1% to about 25% wetting agent, based upon total weight of the tablets. In some embodiments, provided tablets comprise from about 1%, about 3%, about 4%, about 5%, about 10%, about 15%, or about 20% of wetting agent, based upon total weight of given tablets.

In certain embodiments, a wetting agent is a polysorbate. In some embodiments, a wetting agent is polysorbate 80, also known as Tween 80, and is available from Sigma-Aldrich, among other sources. In some embodiments, provided tablets comprise from about 1% to about 25% polysorbate 80, about 1% to about 5%, about 2% to about 5%, about 3%, or to about 4% based upon total weight of given tablet. In certain embodiments, provided tablets comprise from about 1%, about 3%, about 4%, about 5%, about 10%, about 15%, or about 20% polysorbate 80, based upon total weight of given tablets. Without wishing to be bound by any particular theory, polysorbate 80 can also act as an absorption enhancer. Further, without wishing to be bound by any particular theory, polysorbate 80 may facilitate thinning of the mucus layer created in the gastrointestinal tract so that remaining methylnaltrexone in the mucous layer is more readily released for rapid absorption.

Addition of one or more chelating agents may be particularly useful in formulations that include methylnaltrexone, and such agents may provide protection from metal-catalyzed degradation and/or from precipitation of methylnaltrexone. Appropriate chelating agents are known to those skilled in the art, and include any pharmaceutically acceptable chelating agent. Common chelating agents include, but are not limited to ethylenediaminetetraacetic acid (EDTA) and derivatives thereof, ethylene glycol-bis-(2-aminoethyl)-N,N,N',N'-tetraaceticacid (EGTA) and derivatives thereof, diethylenetriaminepentaacetic acid (DTPA) and derivatives thereof, N,N-bis(carboxymethyl)glycine (NTA) and derivatives thereof, nitrilotriacetic acid and derivatives thereof, citric acid and derivatives thereof, niacinamide and derivatives thereof, and sodium desoxycholate and derivatives thereof.

In some embodiments, the chelating agent is selected from the group consisting of EDTA or derivatives thereof. In some embodiments, the chelating agent is selected from the group consisting of calcium EDTA disodium, diammonium EDTA, dipotassium EDTA, disodium EDTA, TEA-EDTA, tetrasodium EDTA, tripotassium EDTA, trisodium EDTA, HEDTA, and trisodium HEDTA, and related salts thereof. In some embodiments, the chelating agent is EDTA disodium, EDTA trisodium, or calcium EDTA disodium. In some embodiments, the chelating agent is calcium EDTA (edetate calcium) or a calcium salt EDTA derivative or calcium EGTA or a calcium salt EGTA derivative. In some embodiments, the chelating agent is calcium EDTA disodium, such as, for example, calcium EDTA disodium hydrate (edetate calcium disodium dihydrate). Calcium EDTA is available from Sigma-Aldrich, among other sources. In some embodiments, provided formulations comprise from about 0.01% to about 5%, about 0.01% to about 4%, about 0.01% to about 3%, 0.01% to about 2%, 0.01% to about 1%, about 0.1% to about 5%, about 0.1% to about 4%, 0.1% to about 4%, about 0.1% to about 3%, about 0.1% to about 2%, about 0.1% to about 1%, or about 0.1% to about 0.5% of the chelating agent, based upon total weight of the formulation. In some embodiments, provided formulations comprise from about 0.1%, about 0.2%, about 0.3%, about 0.4%, about 0.5%, or about 0.6% of the chelating agent, based upon total weight of formulation.

Suitable binders (also referred to as "diluents" and/or "fillers") are known in the art. For example, suitable binders include but are not limited to starch, PVP (polyvinyl pyrrolidone), low molecular weight HPC (hydroxypropyl cellulose), microcrystalline cellulose (e.g., Avicel®), silicified microcrystalline cellulose (Prosolv 50), low molecular weight HPMC (hydroxypropyl methylcellulose), low molecular weight carboxymethyl cellulose, ethylcellulose, alginates, gelatin, polyethylene oxide, acacia, dextrin, sucrose, magnesium aluminum silicate, and polymethacrylates. Fillers include agents selected from the group consisting of microcrystalline cellulose (e.g., Avicel®), starch, lactitol, lactose, a suitable inorganic calcium salt, sucrose, glucose, mannitol, silicic acid, or a combination thereof. In some embodiments, formulations comprise from about 5%, to about 90%, or about 10% to about 50%, or about 10% to about 40%, or about 10% to about 45% binder, based upon total weight of the formulation. In some embodiments, formulations comprise from about 10%, about 15%, about 16%, about 20%, about 24%, about 25%, about 30%, about 35%, about 40%, about 45%, or about 50% binder, based upon total weight of the tablets. In some embodiments, formulations comprise microcrystalline cellulose as a binder. In certain embodiments, formulations comprise the binders, microcrystalline cellulose and silicified microcrystalline cellulose.

In certain embodiments, provided formulations may comprise one or more antioxidants. Such antioxidants include those known to one of ordinary skill in the art. Exemplary antioxidants include ascorbic acid, and salts and esters thereof; citric acid, and salts and esters thereof; butylated hydroxyanisole ("BHA"); butylated hydroxytoluene ("BHT"); tocopherols (e.g., d-alpha tocopherol, dl-alpha tocopherol, d-alpha tocopherol acetate, dl-alpha tocopherol acetate, beta tocopherol, delta tocopherol, gamma tocopherol, and the like), and carotenoids (e.g., vitamin A, lutein, and zeaxanthin). In certain embodiments, a formulation comprises ascorbic acid. In some embodiments, aformulation comprises up to about 10% one or more antioxidants by weight. In some embodiments, a provided formulation comprises about 0.01% to about 5% one or more antioxidants by weight. In some embodiments, a provided formulation comprises about 1.0% to about 10% one or more antioxidants by weight. In certain embodiments, a provided formulation comprises about 1%, about 2%, about 5%, about 6%, about 7%, about 8%, about 9%, or about 10% of one or more antioxidants by weight.

In certain embodiments, formulations may comprise a lubricant. Lubricants, generally, are substances used in solid dosage formulations to reduce friction during compression. Such compounds include, by way of example and without limitation, sodium oleate, sodium stearate, calcium stearate, zinc stearate, magnesium stearate, polyethylene glycol, talc, mineral oil, stearic acid, sodium benzoate, sodium acetate, sodium chloride, and other materials known to one of ordinary skill in the art. In certain embodiments, the lubricant is a stearate salt. In some embodiments, formulations comprise from about 0.1% to about 7%, or about 0.2% to about 1% lubricant, based upon total weight of given formulation. In certain embodiments, the lubricant is magnesium stearate and is available from Sigma-Aldrich, among other sources.

In certain embodiments, formulations may comprise a non-functional coating. For example, in some embodiments, the tablet may comprise a non-functional coating. In some embodiments, the non-functional coating is a seal coat. For example, a suitable seal coating can be applied as a solution (e.g., HPMC solution) at a concentration of about 1% w/w to 25% w/w, and preferably 1% w/w to about 10% w/w. Upon drying, under suitable conditions, initial seal coating is in the range of about 1% w/w to about 3% w/w, or about 2% w/w, of the uncoated tablet. Such a seal coating may comprise a polymer (e.g., HPMC) and may be a commercially available seal coating seal such as Opadry® Clear (Colorcon, Inc.), or HPMC E3. Upon drying, seal coating may be from about 1% to about 10% of weight gain of the total coated formulation. In certain embodiments, the formulation may comprise a coating to prevent disintegration of the dosage form in the oral cavity.

In certain embodiments, the formulation for oral administration comprises (a) about 7% to about 75% of methylnaltrexone bromide, based upon the total weight of the formulation; (b) about 5% to about 80% of an amphiphilic pharmaceutically acceptable excipient, based upon the total weight of the formulation; (c) about 0.01% to about 5% of a chelating agent, based upon the total weight of the formulation; (d) about 1% to about 25% of a wetting agent, based upon the total weight of the formulation; (e) about 5% to about 90% of a binder, based upon the total weight of the formulation; (f) about 1% to about 25% of a disintegrant, based upon the total weight of the formulation; (g) about 0.1% to about 7% of a lubricant, based upon the total weight of the formulation; and optionally, (h) about 0.01% to about 5% of an antioxidant, based upon the total weight of the formulation. In certain embodiments, the methylnaltrexone bromide of the formulation is (R)—N-methylnaltrexone bromide. In certain embodiments, the amphiphilic pharmaceutically acceptable excipient is sodium dodecyl (lauryl) sulfate. In certain embodiments, the chelating agent is a salt of EDTA (e.g., calcium EDTA). In certain embodiments, the wetting agent is polysorbate 80. In certain embodiments, the disintegrant is sodium bicarbonate. In other embodiments, the disintegrant is crospovidone. In certain embodiments, the disintegrant is a combination of sodium bicarbonate and crospovidone. In certain embodiments, the lubricant is magnesium stearate. In certain embodiments, the antioxidant is ascorbic acid. In certain embodiments, the invention provides a tablet formulation for oral administration comprising about 30% methylnaltrexone bromide, about 10% sodium dodecyl sulfate, about 11% microcrystalline cellulose, about 5% crospovidone, about 0.25% calcium EDTA, about 2% polysorbate 80, about 30% Prosolv 50, about 11% sodium bicarbonate, about 2% talc, about 0.5% silicon dioxide colloidal, and about 0.25 magnesium stearate. It will be understood by those skilled in the art that, depending on the manner of making the tablet or other formulation of the invention described herein, the methylnaltrexone may exist paired with bromide, paired with the anion of the amphiphilic pharmaceutically acceptable excipient, or some combination thereof.

Production

In certain embodiments, compositions and formulations are prepared by methods which include an extrusion/spheronization step. In some embodiments, formulations are manufactured via wet-granulation of a provided formulation followed by extrusion/spheronization to form spheroids. Given spheroids are then dried and milled to form a powder which is blended with suitable binder(s) and disintegrant(s).

The resulting mixture is then milled and blended with a suitable lubricant and pressed into tablets. In certain embodiments, a non-functional coating is applied.

In some embodiments, tablets are prepared by methods which do not include extrusion/spheronization steps and, in accordance with such methods, are manufactured via wet-granulation. Once dried, the granulation is milled to form a granular powder which is blended with suitable binder(s) and disintegrant(s). The resulting mixture is then milled and blended with a suitable lubricant and pressed into tablets. In certain embodiments, a non-functional coating is applied.

Unit Dosage Form

Formulations of methylnatrexone may be prepared as a unit dosage form. Indeed, a tablet is typically a unit dosage form. In some embodiments, a unit dosage form contains 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, or 1500 mg of methylnaltrexone bromide. In some embodiments, a unit dosage form contains between 50 mg and 900 mg, inclusive, or between 150 mg and 450 mg, inclusive, of methylnaltrexone bromide. In some embodiments, a unit dosage form contains 50 mg, 75 mg, 150 mg, 225 mg, 300 mg, 450 mg, 600 mg, or 900 mg of methylnaltrexone bromide. In some embodiments, the unit dosage form comprises methylnaxtrexone and an amphiphilic pharmaceutically acceptable excipient, e.g., sodium dodecyl (lauryl) sulfate (also known as SDS or SLS).

Administration

Compositions and formulations may be administered to a patient as required to provide an effective amount of methylnaltrexone. In certain embodiments, the patient is orally administered methylnaltrexone or a formulation thereof at least once a day. In other embodiments, the patient is orally administered methylnaltrexone or a formulation thereof up to once a day. In certain embodiments, the patient is orally administered methylnaltrexone or a formulation thereof not more than once a day. In certain embodiments, the patient is orally administered methylnaltrexone or a formulation thereof as needed. In certain embodiments, the patient is orally administered methylnaltrexone or a formulation thereof as needed, but not more than once a day. For example, a unit dosage form of a provided formulation may be orally administered to a patient in a single day, for example, a unit dosage of about 150 mg, 300 mg, or 450 mg methylnaltrexone bromide or an equivalent molar amount of methylnaltrexone. In some embodiments, the present invention provides a method for treating an opioid-induced side effect in a patient in need thereof, comprising the step of orally administering to said patient one or more tablets of the present invention wherein said tablet provides about 150 mg, 300 mg, or 450 mg of methylnaltrexone or an equivalent molar amount of methylnaltrexone bromide, e.g., methylnaltrexone and a amphiphilic pharmaceutically acceptable excipient such as sodium dodecyl (lauryl) sulfate (also known as SDS or SLS), sodium heptyl sulfate, sodium heptyl sulfonate, perfluorooctanesulfonate (PFOS), and the like. In certain embodiments, a single tablet formulation of the present invention provides about 25 mg, about 50 mg, about 75 mg, about 100 mg, about 125 mg, about 150 mg, about 300 mg, or about 450 mg of methylnaltrexone bromide, or equivalent moles of another salt form, or methylnaltrexone and an amphiphilic pharmaceutically acceptable excipient such as sodium dodecyl (lauryl) sulfate (also known as SDS or SLS).

As defined above, in certain embodiments the term "effective amount," as used in connection with an amount of methylnaltrexone, means an amount of methylnaltrexone sufficient to achieve laxation in a patient. In some embodiments, an effective amount means an amount of methylnaltrexone sufficient to achieve laxation in a patient within about 24 hours, within about 12 hours, within about 8 hours, within about 5 hours, within about 4 hours, within about 3 hours, within about 2 hours, or within about 1 hours of administration to said patient. In some embodiments, effective amount means an amount of methylnaltrexone sufficient to achieve laxation within about 4 hours of administration to the patient. In some embodiments, effective amount means an amount of methylnaltrexone sufficient to achieve laxation within about 4 hours of administration to the patient for at least 99%, at least 95%, at least 90%, at least 85%, at least 80%, at least 75%, or at least 50% of all doses administered. In some embodiments, effective amount means an amount of methylnaltrexone sufficient to achieve laxation within about 4 hours of administration to the patient for all doses administered during first four weeks of dosing.

In some embodiments, the formulations are administered to a fasted patient. As used herein, the term "fasted" means that the patient has not eaten any food for at least 2 hours, at least 4 hours, for at least 6 hours, for at least 8 hours, for at least 10 hours, or for at least 12 hours prior to administration of a provided formulation. In certain embodiments, the term "fasted" means an overnight fast. It is believed that improved effects will be seen in fasted patients than in fed patients. These effects may be magnified in patients administered methylnatrexone in a provided tablet as compared with patients administered the same dose in capsule form. Thus, administration of a provided methylnaltrexone tablet formulation to a patient in a fasted state is believed to be advantageous.

In other embodiments, the formulations are administered to a patient that has not fasted. Therefore, there is no requirement that the patient not have eaten before methylnaltrexone is administered.

Combination Products and Combined Administration

It will also be appreciated that provided compositions and formulations can be employed in combination therapies, that is, provided formulations can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated."

In some embodiments, methylnaltrexone or an ion pair or formulation of the invention and one or more other active agents may be administered together in a single formulation (e.g., unit dosage form); in other embodiments, methylnaltrexone and one or more other active agents may be administered as separate formulations. In certain embodiments, methylnaltrexone and/or one or more other active agent may be administered in multiple doses.

In some embodiments, the other active agent administered in combination with a methylnaltrexone ion pair or formulation of the invention is an opioid. Combination therapy of methylnaltrexone and an opioid can allow simultaneous relief of pain and minimization of opioid-associated side effects (e.g., gastrointestinal effects (e.g., delayed gastric emptying, altered GI tract motility)). Accordingly and in certain embodiments, the present invention provides a unit dosage form comprising a combination of methylnaltrexone with an opioid together in a single layer dosage form (e.g., tablet). In some embodiments, such a unit dosage form may be a bi-layer tablet comprising methylnaltrexone in one layer and an opioid in another layer. In a specific embodiment, the combination unit dosage form is suitable for oral administration.

Opioids useful for analgesia are known in the art. For example, opioid compounds include, but are not limited to, alfentanil, anileridine, asimadoline, bremazocine, burprenorphine, butorphanol, codeine, dezocine, diacetylmorphine (heroin), dihydrocodeine, diphenoxylate, ethylmorphine, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, nicomorphine, opium, oxycodone, oxymorphone, papavereturn, pentazocine, propiram, propoxyphene, remifentanyl, sufentanil, tilidine, trimebutine, and tramadol. In some embodiments the opioid is at least one opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, nicomorphine, oxycodone, oxymorphone, papavereturn, pentazocine, propiram, propoxyphene, sufentanil and/or tramadol. In certain embodiments of the present invention, the opioid is selected from morphine, codeine, oxycodone, hydrocodone, dihydrocodeine, propoxyphene, fentanyl, tramadol, and mixtures thereof. In a particular embodiment, the opioid is loperamide. In other embodiments, the opioid is a mixed agonist such as butorphanol. In some embodiments, the subjects are administered more than one opioid, for example, morphine and heroin or methadone and heroin.

Typically, the amount of other active agent(s) administered in combination therapy may be no more than the amount that would normally be administered in monotherapy with the relevant agent(s). In certain embodiments, the amount of other active agent administered in combination therapy may be less than that normally administered in monotherapy with the relevant agent(s). For example, in certain embodiments of the present invention, the amount of additional active agent can range from about 50% to 100% of the amount normally present in a formulation comprising that compound as the only therapeutic agent.

In certain embodiments, formulations may also be used in conjunction with and/or in combination with conventional therapies for gastrointestinal dysfunction to aid in the amelioration of constipation and bowel dysfunction. For example, conventional therapies include, but may not be limited to functional stimulation of the intestinal tract, stool softening agents, laxatives (e.g., diphelymethane laxatives, cathartic laxatives, osmotic laxatives, saline laxatives), bulk forming agents and laxatives, lubricants, intravenous hydration, and nasogastric decompression.

Uses and Kits of Compositions and Formulations

The present invention provides pharmaceutically acceptable formulations as described herein comprising methylnaltrexone for oral administration useful for the delivery of such compounds in any context in which such delivery is desirable. In certain embodiments, provided formulations are useful for the delivery of methylnaltrexone in antagonizing undesirable side effects of opioid analgesic therapy (e.g., gastrointestinal effects (e.g., delayed gastric emptying, altered GI tract motility)). Furthermore, formulations may be used as to treat subjects having disease states that are ameliorated by binding μ opioid receptors, or in any treatment wherein temporary suppression of the μ opioid receptor system is desired (e.g., ileus). In certain embodiments of the present invention, methods of use of provided formulations are in human subjects.

Accordingly, administration of provided formulations may be advantageous for treatment, prevention, amelioration, delay or reduction of side effects of opioid use, such as, for example, gastrointestinal dysfunction (e.g., inhibition of intestinal motility, constipation, GI sphincter constriction, nausea, emesis (vomiting)), biliary spasm, opioid bowel dysfunction, colic, dysphoria, pruritis, urinary retention, depression of respiration, papillary constriction, cardiovascular effects, chest wall rigidity and cough suppression, depression of stress response, and immune suppression associated with use of narcotic analgesia, or combinations thereof. Use of a formulationmay thus be beneficial from a quality of life standpoint for subjects undergoing use of opioids, as well as to reduce complications arising from chronic constipation, such as hemorrhoids, appetite suppression, mucosal breakdown, sepsis, colon cancer risk, and myocardial infarction.

In some embodiments, provided formulations are useful for administration to a subject undergoing acute opioid use. In some embodiments, provided formulations are useful for administration to patients suffering from post-operative gastrointestinal dysfunction.

In certain embodiments, provided formulations are also useful for administration to subjects undergoing chronic opioid use (e.g., terminally ill patients receiving opioid therapy such as an AIDS patient, a cancer patient, a cardiovascular patient; subjects receiving chronic opioid therapy for pain management; subjects undergoing opioid therapy for maintenance of opioid withdrawal). In some embodiments, the subject is a subject using opioid therapy for chronic pain management. In certain embodiments, the pain is non-malignant pain (e.g., back pain, neuropathic pain, pain associated with fibromyalgia, osteoarthritis). In some embodiments, the subject is a terminally ill patient. In other embodiments the subject is a person undergoing opioid withdrawal maintenance therapy.

In certain embodiments, the formulations provided herein are administered to subjects that have been selected for treatment with methylnaltrexone. In specific embodiments, the subject is selected based on the subject having an increased risk for developing one or more of the conditions set forth above. In another embodiment, the subject is selected based on the use of opioid therapy for pain management, or based on having one or more of the conditions set forth herein. In certain embodiments, the subject is constipated or has a history of constipation due to opioid therapy. In one embodiment, a constipated subject has not had a bowel movement in the previous three days. In one embodiment, a constipated subject has had less than three bowel movements in the previous week. In certain embodiments, a constipated subject has had less than three rescue-free bowel movements per week on average over the last four consecutive weeks, and one or more of the following: (a) hard or lumpy stools, (b) straining during bowel movements, and/or (c) sensation of incomplete evacuation after bowel movements.

In certain embodiments, the subject is selected for treatment with a methylnaltrexone formulation described herein based on the use of opioids, e.g., for non-malignant pain. The subject may be using opioids intermittently or regularly. In one embodiment, the subject that is selected has been taking opioids as needed. In one embodiment, the subject that is selected has been taking opioids for less than one week. In one embodiment, the subject that is selected has been taking opioids over the course of at least one week. In another embodiment, the subject that is selected has been taking opioids over the course of at least two weeks. In another embodiment, the subject that is selected has been taking opioids over the course of at least three weeks. In another embodiment, the subject that is selected has been taking opioids over the course of at least four weeks. In another embodiment, the subject that is selected has been taking opioids over the course of at least three months. In another embodiment, the subject that is selected has been taking opioids over the course of at least six months. In another embodiment, the subject that is selected has been taking opioids over the course of at least twelve months. In another embodiment, the subject that is selected has been taking opioids over the course of more than one year. In another embodiment, the subject that is selected has been taking opioids at least every other day over the course of at least two weeks. In one embodiment, the subject that is selected has been receiving at least 7 doses>25 mg of oral morphine equivalents over at least 14 days. In one embodiment, the subject that is selected has been receiving a daily dose of >50 mg of oral morphine equivalents for at least 14 days. In one embodiment, the subject that is selected is constipated due to opioid therapy and has been receiving a daily dose of >50 mg of oral morphine equivalents for at least 14 days. In certain embodiments, the subject has been receiving a daily dose of >50 mg of oral morphine equivalents for at least 14 days; and has had less than three (3) rescue-free bowel movements per week on average over the least four consecutive weeks that were associated with one or more of the following: (a) a Bristol Stool Form Scale type 1 or 2 for at least 25% of the rescue-free bowel movements, (b) straining during at least 25% of the rescue-free bowel movements; and/or (c) a sensation of incomplete evacuation after at least 25% of the rescue-free bowel movements. A rescue-free bowel movement refers to a bowel movement associated with no laxative use within the 24 hours prior to the bowel movement.

In certain embodiments, the subject selected for treatment with a methylnaltrexone formulation described herein is a subject suffering from opioid-induced constipation. In certain embodiments, the subject selected for treatment with a methylnaltrexone formulation described herein is a subject with advanced illness who is receiving palliative care and is suffering from opioid-induced constipation. In certain embodiments, the subject selected for treatment with a methylnaltrexone formulation described herein is a subject with advanced illness who is receiving palliative care and is suffering from opioid-induced constipation where response to laxative therapy (e.g., bisacodyl, senokot, docusate) has not been sufficient. In certain embodiments, the subject selected for treatment with a methylnaltrexone formulation described herein is a subject with non-malignant pain who is suffering from opioid-induced constipation. In certain embodiments, the subject selected for treatment with a methylnaltrexone formulation described herein is a subject with non-malignant pain who is suffering from opioid-induced constipation where response to laxative therapy (e.g., bisacodyl, senokot, docusate) has not been sufficient. In certain embodiments, the subject selected for treatment with a methylnaltrexone formulation described herein has not responded to standard laxative therapy. In certain embodiments, the subject selected for treatment with a methylnaltrexone formulation described herein has responded to standard laxative therapy. In certain embodiments, the subject selected for treatment with a methylnaltrexone formulation described herein is concurrently administered laxative therapy.

Alternative or additional uses for provided formulations described herein are useful for treating effects of opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of provided formulations include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases.

In certain embodiments, provided formulations may be used in methods for preventing, inhibiting, reducing, delaying, diminishing or treating gastrointestinal dysfunction, including, but not limited to, irritable bowel syndrome, opioid-induced bowel dysfunction, colitis, post-operative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection), hysterectomy), and delayed absorption of orally administered medications or nutritive substances.

Provided formulations are also useful in treatment of conditions including cancers involving angiogenesis, immune suppression, sickle cell anemia, vascular wounds, and retinopathy, treatment of inflammation associated disorders (e.g., irritable bowel syndrome), immune suppression, chronic inflammation.

In other embodiments, provided formulations and unit dose forms are useful in preparation of medicaments, including, but not limited to medicaments useful in the treatment of side effects of opioid use, including gastrointestinal side effects (e.g., inhibition of intestinal motility, GI sphincter constriction, constipation), nausea, emesis, vomiting, dysphoria, pruritis, or a combination thereof. Provided formulations are useful for preparations of medicaments, useful in treatment of patients receiving acute opioid therapy (e.g., patients suffering from post-operative gastrointestinal dysfunction receiving acute opioid administration) or subjects using opioids chronically (e.g., terminally ill patients receiving opioid therapy such as an AIDS patient, a cancer patient, a patient with cardiovascular disease; subjects receiving chronic opioid therapy for pain management (malignant or non-malignant pain); or subjects undergoing opioid therapy for maintenance of opioid withdrawal). Still further, preparation of medicaments useful in the treatment of pain, treatment of inflammatory conditions such as inflammatory bowel syndrome, treatment of infectious diseases, treatment of diseases of the musculoskeletal system such as osteoporosis, arthritis, osteitis, periostitis, myopathies, treatment of autoimmune diseases and immune suppression, therapy of post-operative gastrointestinal dysfunction following abdominal surgery (e.g., colectomy (e.g., right hemicolectomy, left hemicolectomy, transverse hemicolectomy, colectomy takedown, low anterior resection), idiopathic constipation, and ileus (e.g., post operative ileus, post partum ileus), and treatment of disorders such as cancers involving angiogenesiss, chronic inflammation and/or chronic pain, sickle cell anemia, vascular wounds, and retinopathy.

In still further embodiments, veterinary applications (e.g., treatment of domestic animals, e.g., horse, dogs, cats) of use of provided formulations are provided. Thus, use of provided formulations in veterinary applications analogous to those discussed above for human subjects is contemplated. For example, inhibition of equine gastrointestinal motility, such as colic and constipation, may be fatal to a horse. Resulting pain suffered by the horse with colic can result in a death-inducing shock, while a long-term case of constipation may also cause a horse's death. Treatment of equines with peripheral opioid receptor antagonists has been described, e.g., in U.S. Patent Publication No. 2005/0124657, published Jan. 20, 2005, which is incorporated herein by reference.

Still further encompassed by the invention are pharmaceutical packs and/or kits comprising formulations described herein, and a container (e.g., a foil or plastic package, or other suitable container). Optionally instructions for use are additionally provided in such kits.

In order that the invention described herein may be more fully understood, the following examples are set forth. It should be understood that these examples are for illustrative purposes only and are not to be construed as limiting this invention in any manner.

All features of each of the aspects of the invention apply to all other aspects *mutatis mutandis*. The contents of all references, patents, pending patent applications and published patents, cited throughout this application are hereby expressly incorporated by reference.

EXAMPLES

Example 1

Methylnaltrexone bromide may be prepared according to the methods described in detail in international PCT Patent Application publication number, WO 2006/127899, or obtained from commercial sources such as Covidien, Saint Louis, Mo. Formulations containing methylnaltrexone were prepared using pharmaceutically acceptable excipients. Spheroids containing methylnaltrexone were prepared. Capsules were prepared by filling capsules with spheroids. Some capsules were prepared to contain enterically coated spheroids, which spheroids dissolve only after passing through the stomach. The capsules, without an enteric coat, or after dissolution of the enteric coat, will dissolve over 10-30 minutes. Tablets also were prepared from spheroids, using conventional techniques. The tablets dissolve in under 10 minutes.

The spheroids were prepared by a wet granulation process followed by extrusion and spheronization, as described in the following general method. Methylnaltrexone bromide and pharmaceutically acceptable excipients were combined in an aqueous solution. Water was added until wet mass suitable for extrusion was obtained. The wet mass was passed through an extruder, and the extrudate was spheronized in a spheronizer.

The resulting spheroids were dried in a fluid bed drier and passed through a screen. The uncoated spheroids were stored in appropriate container.

Example 2

Administration of Capsules Containing Enterically Coated Methylnaltrexone Spheroids Capsules containing enterically coated spheroids of methylnaltrexone as described in Example 1 were tested in patients suffering from opioid-induced constipation. The patients in this study were not chronic methadone maintenance patients. The patients had chronic non-malignant (not cancer) pain where the non-malignant condition underlying the chronic pain (e.g., osteoarthritis, back pain, neuropathic pain) had a documented history of at least 2 months before screening, stable pain for at least 1 month. The patients were on opioids for at least one month and at a daily dose of greater than or equal to 20 mg of morphine equivalents per day for at least two weeks before the screening visit and during the screening visit period with no anticipated changes during the study. The patients also had a history of constipation due to opioid use for at least one month before the screening visit. Constipation defined as less than 3 bowel movements per week on average and 1 or more of the following: (i) hard or lumpy stools for at least 25% of bowel movements, (ii) a sensation of incomplete evacuation following at least 25% of bowel movements, (iii) straining during at least 25% of bowel movements.

Patients were administered enterically coated methylnaltrexone capsules containing 10 mg, 50 mg, 150 mg, 300 mg or 450 mg of methylnaltrexone. The average peak plasma level of methylnaltrexone resulting from the doses was as follows: (i) for 10 mg, less than 1 ng/ml, (ii) for 50 mg, less than 5 ng/ml, (iii) for 150 mg, less than 5 ng/ml, (iv) for 300 mg, less than 10 ng/mL, and (v) for 450 mg, less than 20 ng/mL. These capsules containing enterically coated preparations of methylnaltrexone were not effective for treating opioid-induced constipation. They did not induce laxation and did not cause more bowel movements in patients relative to controls.

Example 3

Administration of Capsules Containing Methylnaltrexone Not Enerically Coated

Capsules containing spheroids of methylnaltrexone, but without the enteric coating, prepared as described in Example 1, were tested in patients receiving opioids for non-malignant pain. The patients in this study were not chronic methadone maintenance patients. The patients were selected on the basis of the same criteria as the criteria used in Example 2, except the minimum daily dose of opioids was equal to or greater than 30 mg, instead of 20 mg of morphine equivalents. Doses of 150 mg, 300 mg, 450 mg, and 600 mg were tested. These doses resulted in average peak plasma levels of between about 15 and 40 ng/ml, on the order of 3 or more times lower than the average peak plasma levels associated with effective doses of subcutaneous methylnaltrexone injection. These capsules containing spheroids without the enteric coating did not induce laxation and did not cause more bowel movements in this patient population relative to controls.

Administration of Tablets Containing Methylnaltrexone Not Enterically Coated

Tablets containing spheroids of methylnaltrexone, without an enteric coating, prepared as described in Example 1, were tested in patients receiving opioids for non-malignant pain.

The patients in this study were not chronic methadone maintenance patients. The patients were selected on the basis of the same criteria as the criteria used in Example 3. Doses of 150 mg, 300 mg, 450 mg, and 600 mg were tested. These doses resulted in average peak plasma levels of between about 7 and 40 ng/ml. These tablets without an enteric coating showed statistically significant activity at one dose, but did not consistently induce laxation across all doses.

Both tablets and capsules containing uncoated spheroids had similar compositions except that spheroids were compressed with pharmaceutically acceptable excipients to form tablets, while spheroids were encapsulated into hard gelatine shells to prepare capsules. Once contacted with an aqueous medium, the tablets disintegrated immediately and almost all the drug dissolved in less than 10 minutes. In contrast, it took 10 minutes for the capsule shells to dissolve and at least 30 minutes for the complete dissolution of the drug from the capsules. (FIG. 1) Plasma levels associated with both dosage forms containing uncoated spheroids were variable (tablets produced more consistent average peak plasma levels relative to the capsule) and overlapping among the subjects.

Example 4

Determination of Partition Coefficient

Ion pairs of methylnaltrexone with amphiphilic pharmaceutically acceptable excipients were prepared and the apparent octanol-water partition coefficient (APC) was measured and compared to that of methylnaltrexone bromide. A predetermined amount of each of MNTX-heptyl sulfate and MNTX-dodecyl sulfate was dissolved in 2 mL of 1-octanol that was saturated with water. Two mL of water that was saturated with 1-octanol was added to each MNTX salt solution. The mixtures were shaken overnight at room temperature, and 1 mL of the 1-octanol phase was then diluted to 10 mL with the mobile phase used for chromatographic (HPLC) analysis of the samples. And 1 mL of the aqueous phase was diluted to 5 mL with the mobile phase. The samples were then analyzed by HPLC to determine the apparent partition coefficient and logP for each MTNX salt. The pH of the aqueous phases for each of the salts was between 4.5 and 6.8. (The reported partition coefficient for MNTX is 0.0025 and the LogP is −1.605.)

| MNTX Salt | mg used | APC | Log P |
| --- | --- | --- | --- |
| MNTX-heptyl sulfate | 21.323 | 1.961 | 0.292 |
| MNTX-dodecyl sulfate | 15.175 | 32.014 | 1.505 |
| MNTX-laurate | 12.843 | 2.131 | 0.328 |

Example 5

Preparation of Tablets Containing Methylnaltrexone Bromide and Sodium Dodecyl Sulfate The present Example describes the preparation of tablets containing methylnaltrexone, sodium dodecyl sulfate (SDS), and an effervescent disintegrant (sodium bicarbonate). The quantitative formulation of methylnaltrexone (150 mg) tablets is provided in Table 5-1.

TABLE 5-1

Composition of Methylnaltrexone Bromide 150 mg Uncoated Tablets with SDS

| Ingredient | % w/w | Unit Dose mg/Tablet |
| --- | --- | --- |
| Granulation | | |
| Methylnaltrexone Bromide[a] | 28.95 | 150.00 |
| Microcrystalline Cellulose | 11.30 | 58.54 |
| Sodium Dodecyl Sulfate | 9.65 | 50.00 |
| Crospovidone | 1.83 | 9.48 |
| Polysorbate 80 (vegetable grade) | 2.07 | 10.73 |
| Edetate Calcium Disodium Dihydrate | 0.28 | 1.46 |
| Purified Water[b] | NA | 40.03 |
| Blend | | |
| Silicified Microcrystalline Cellulose | 28.95 | 150.00 |
| Crospovidone | 3.00 | 15.52 |
| Sodium Bicarbonate | 11.30 | 58.54 |
| Talc | 1.93 | 10.00 |
| Colloidal Silicon Dioxide | 0.49 | 2.50 |
| Final Blend | | |
| Magnesium Stearate | 0.25 | 1.28 |
| Total | 100.0% | 518.05 mg |

[a]Based upon 100% purity "as is", quantity may be adjusted based on actual potency, with corresponding adjustments made to microcrystalline cellulose.
[b]Removed by drying. Does not appear in final dosage form.

Method of Manufacture and Packaging: Procedure
1. Blend methylnaltrexone bromide, microcrystalline cellulose, sodium dodecyl sulfate (SDS), and crospovidone in a granulator.
2. Make a solution containing edetate calcium disodium and polysorbate 80 in purified water.
3. While mixing blend from Step 1, add the edetate calcium disodium/polysorbate 80 solution for approximately 4 minutes. Additional water might be added to obtain proper granulation. Note: the granulation steps may be completed in sub-batches to obtain larger batch sizes.
4. Dry the granulation.
5. Using suitable mill, mill the granulation from #4.
6. Add material from #5 to a suitable blender.
7. Record the yield for milling and adjust the levels of excipients for the final blend.
8. Optional screening of crospovidone, silicified microcrystalline cellulose, sodium bicarbonate, talc, silicon dioxide, and magnesium stearate through appropriate sieve.
9. Add to the blender, crospovidone, sodium bicarbonate, talc, and silicified microcrystalline cellulose, and blend
10. Optionally screening the blend of Step 9 through appropriate sieve and add to the blender and blend.
11. Optionally, take a portion of the blend, add to the silicon dioxide and bag blend.
12. Optionally, transfer the pre-mix of the silicon dioxide and add to the blender and blend.
13. Take a portion of the blend, add to the magnesium stearate and bag blend. Note: Step 13 may not be required for batches larger than 50 kg.
14. Transfer the pre-mix magnesium stearate and blend to the blender and blend.
15. Record the final yield of blend.
16. Compress the final blend from step 15 using a suitable compression machine fitted with tooling which can produce tablets of the required specification.
17. Weigh the yield of acceptable tablets.

Example 6

Tablets including methylnaltrexone bromide (150 mg), sodium dodecyl sulfate (SDS), and sodium bicarbonate were manufactured using the method described in Example 5. The tablet was placed in a dissolution apparatus with paddles at 100 rpm in 900 mL of 0.1N HCl at 37° C. Samples were then removed at specified times points and analyzed by HPLC. The dissolution rates of two tablets were determined. The dissolution profile of the SDS tablet with sodium bicarbonate is shown in FIG. 2. Greater than 90% of the methylnaltrexone from the tablets was dissolved within 11 minutes.

Example 7

Administration of Provided Formulations in GI-Physiology Altered Dogs

Oral bioavailability and pharmacokinetic profiles of tablets containing methylnatraxone bromide (150 mg), sodium dodecyl sulphate (SDS) and sodium bicarbonate, prepared as described in Example 5, were compared with tablets containing uncoated spheroids of methylnaltrexone, but not containing an amphiphilic pharmaceutically acceptable carrier or an effervescent disintegrant, prepared as described in Example 1. Using GI-physiology altered male beagle dogs, atropine (~20 µg/kg; IV) and pentagastrin (~10 µg/kg; 1M) were administered 15 minutes prior to formulation administration and another dose of pentagastrin (10 µg/kg; IM) was administered 30 minutes post dose. Atropine slows down canine GI motility and pentagastrin decreases pH resulting in GI conditions almost similar to that of humans. The formulations (150 mg MNTX) were dosed to six dogs (9.4-13.7 kg) via oral administration following an overnight fast and blood samples were drawn at 0 (predose), 0.5, 1, 2, 3, 4, 6, 8, 12, 24, and 48 hours after dosing; plasma was separated and assayed for methylnaltrexone content.

Individual dog plasma methylnaltrexone concentration-time profiles were subjected to non-compartmental pharmacokinetic analyses (WinNonlin, Model 200). The results are summarized in Table 7-1 below.

TABLE 7-1

Individual and Mean (±SD) MNTX Pharmacokinetic Parameters in GI Physiology Regulated Dogs Following a Single Oral Administration of 150 mg MNTX Prototype Formulations

| Formulation | Dog | Dose (mg/kg) | $C_{max}$ (ng/mL) | $AUC_{0-\infty}$ (hr * ng/mL) |
|---|---|---|---|---|
| Tablet no SDS | Mean | 15.2 | 565 | 2091 |
|  | SD | ±0.46 | ±206 | ±572 |
| Tablet with | Mean | 15.7 | 978 | 2983 |
| SDS | SD | ±0.91 | ±322 | ±720 |

As summarized in the above Table 7-1, oral administration of prototype tablet formulation containing the ion-pairing agent sodium dodecyl (lauryl) sulfate resulted in qualitatively greater methylnaltrexone systemic exposures than tablets containing no ion pairing agent.

Example 8

This example reports on the efficacy of methylnaltrexone in the SDS tablet formulation at a dose of 300 and 450 mg administered orally to subjects with chronic non-malignant pain. Subjects enrolled in this study had to have a history of constipation due to opioid use for at least one month before the screening visit. The study was a phase 1, open-label, single dose, inpatient studies. Subjects received methylnaltrexone as a single dose (2×150 mg or 3×150 mg) of the SLS tablet formulation after an overnight fast of at least 10 hours. The dose was taken orally with 240 mL of room temperature water at approximately 0800 hours on day 1. Opioid medication was provided at approximately the same time every day. Each subject participated in the study for approximately 3 weeks. This included a screening evaluation within 3 weeks before test article administration and a 2 day/1 night inpatient period.

The results are presented in FIG. 3. This figures shows a plot of the comparison between time and the percentage of patients having a first laxation response in patients with chronic malignant pain administered a methylnaltrexone (300 mg and 450 mg) SDS tablet after a 10 hour fast. The SLS tablet formulation resulted in increases in percentage laxation within 4 hours and within 24 hours in subject patients.

In Example 8, the percentage of patients who laxated within 4 hours of receiving a single initial dose of 450 mg of the SDS formulation of the invention was approximately 41%. In Example 8, the percentage of patients who laxated within 24 hours of receiving a single initial dose of 450 mg of the SDS formulation of the invention was approximately 72%.

The foregoing study was not designed to establish statistical significance of laxation. There was no placebo group. It is noted that historically in larger studies of chronic nonmalignant pain patients designed with similar but more rigorous inclusion/exclusion criteria, the percentage of subjects receiving placebo who laxated within 4 hours was on the order of about 9%-13%. One of skill in the art will appreciate that the placebo response in the present study could be different from the previous studies due to such factors as the smaller study size and different inclusion/exclusion criteria. Without wishing to be bound by any theory of the invention, it is believed that there may be a dual mechanism involved in achieving laxation when an oral dose is administered and that the plasma levels required to achieve laxation when dosing orally may be less than those required when dosing subcutaneously.

One skilled in the art will readily ascertain the essential characteristics of the invention and understand that the foregoing description and Examples are illustrative of practicing the provided invention. Those skilled in the art will be able to ascertain using no more than routine experimentation, many variations of the detail presented herein may be made to the specific embodiments of the invention described herein without departing from the spirit and scope of the present invention.

What is claimed is:

1. A pharmaceutical composition for oral administration comprising a solid dosage of (i) methylnaltrexone, or a pharmaceutically acceptable salt thereof, and (ii) an amphiphilic pharmaceutically acceptable excipient, and wherein the composition comprises from about 7% to about 75% methylnaltrexone cation and an anion of the amphiphilic pharmaceutically acceptable excipient based upon the total weight of the composition and wherein the composition in solution has an apparent octanol/water partition coefficient for methylnaltrexone of at least 0.25 at a pH between 1 and 4.

2. The pharmaceutical composition according to claim 1, wherein the amphiphilic pharmaceutically acceptable excipient has a $pK_a$ of 3 or less.

3. The pharmaceutical composition according to claim 1, wherein the amphiphilic pharmaceutically acceptable excipient comprises a sulfate (—OSO$_3^-$) group.

4. The pharmaceutical composition according to claim 1, wherein the amphiphilic pharmaceutically acceptable excipient comprises a saturated or unsaturated, branched or unbranched, cyclic or acyclic C$_{4-30}$ aliphatic group that is optionally substituted.

5. The pharmaceutical composition according to claim 1, wherein the amphiphilic pharmaceutically acceptable excipient comprises a saturated, unbranched, acyclic, unsubstituted C$_{4-30}$ alkyl group.

6. The pharmaceutical composition according to claim 1, wherein the amphiphilic pharmaceutically acceptable excipient comprises a saturated, unbranched, acyclic, unsubstituted C$_{7-15}$ alkyl group.

7. The pharmaceutical composition according to claim 1, wherein the amphiphilic pharmaceutically acceptable excipient comprises a C$_{12}$ n-alkyl group.

8. The pharmaceutical composition of claim 1, further comprising a disintegrant.

9. The pharmaceutical composition of claim 8, wherein at least 50% of the composition dissolves in a dissolution apparatus with paddles at 100 rpm in 900 mL of 0.1 N HCl at 37° C. within about 15 minutes.

10. The composition of claim 8, wherein at least 75% of the composition dissolves in a dissolution apparatus with paddles at 100 rpm in 900 mL of 0.1 N HCl at 37° C. within about 15 minutes.

11. The composition according to claim 1, wherein the apparent partition coefficient is at least 1.

12. The composition according to claim 11, wherein the apparent partition coefficient is at least 10.

13. The composition according to claim 12, wherein the apparent partition coefficient is at least 20.

14. The composition according to claim 1, wherein the amphiphilic pharmaceutically acceptable excipient is an anionic surfactant.

15. The composition according to claim 8, wherein the disintegrant is an effervescent disintegrant.

16. The composition according to claim 15, wherein the disintegrant is a bicarbonate.

17. The composition according to claim 1, wherein the composition is a tablet.

18. The composition according to claim 1, wherein the composition is a tablet comprising at least one or more of a binder, a chelating agent, a wetting agent, a lubricant, a non-functional coating, or an antioxidant, and combinations thereof.

19. The composition according to claim 18, wherein the composition comprises a chelating agent.

20. The composition according to claim 19, wherein the chelating agent is a salt of EDTA.

21. The composition according to claim 20, wherein the chelating agent is calcium EDTA disodium.

22. The composition according to claim 18, wherein the composition comprises a lubricant.

23. The composition according to claim 22, wherein the lubricant is magnesium stearate.

24. The composition according to claim 18, wherein the composition comprises an antioxidant.

25. The composition according to claim 24, wherein the antioxidant is ascorbic acid.

26. The composition according to claim 18, wherein the lubricant is magnesium stearate.

27. The composition according to claim 18, wherein and the antioxidant is ascorbic acid.

28. The pharmaceutical composition of claim 1, wherein the composition comprises a compound of formula (I):

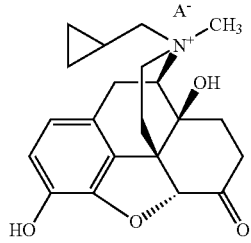

wherein A$^-$ is an anion of the amphiphilic pharmaceutically acceptable excipient.

29. The pharmaceutical composition of claim 1, wherein the amphiphilic pharmaceutically acceptable excipient comprises dodecyl sulfate.

30. The pharmaceutical composition of claim 1, wherein the composition further comprises at least one or more of a binder, a chelating agent, a wetting agent, a lubricant, a non-functional coating, or an antioxidant, and combinations thereof.

31. The pharmaceutical composition of claim 30, wherein the composition further comprises a lubricant.

* * * * *